United States Patent [19]

Pryor et al.

[11] Patent Number: 4,493,554

[45] Date of Patent: * Jan. 15, 1985

[54] METHOD AND APPARATUS FOR DETERMINING PHYSICAL CHARACTERISTICS OF OBJECTS AND OBJECT SURFACES

[75] Inventors: Timothy R. Pryor; Omer L. Hageniers; Walter J. Pastorius; Nicholas Liptay-Wagner; Donald A. Clarke, all of Windsor, Canada

[73] Assignee: Diffracto, Windsor, Canada

[*] Notice: The portion of the term of this patent subsequent to Dec. 15, 1998 has been disclaimed.

[21] Appl. No.: 295,577

[22] Filed: Aug. 24, 1981

Related U.S. Application Data

[63] Continuation of Ser. No. 15,792, Feb. 27, 1979, Pat. No. 4,305,661.

[51] Int. Cl.³ .................... G01N 21/17; G01N 21/88; G01B 11/30
[52] U.S. Cl. .................... 356/241; 250/562; 356/237; 356/394
[58] Field of Search ............. 356/241, 371, 375–376, 356/378, 384, 387, 390, 394, 237; 350/506, 96.26; 250/562–563, 572; 364/507; 358/106

[56] References Cited

U.S. PATENT DOCUMENTS

| | | | |
|---|---|---|---|
| 1,791,794 | 2/1931 | Chesney | 350/96.26 |
| 1,932,470 | 10/1933 | Lehmann | 350/506 |
| 3,019,346 | 1/1962 | Laycak | 250/562 |
| 3,221,593 | 12/1965 | Ferris | 350/506 |
| 3,551,061 | 12/1970 | Glowa | 356/241 |
| 3,618,063 | 11/1971 | Johnson | 250/563 |
| 3,705,771 | 12/1972 | Friedman et al. | 356/39 |
| 3,749,496 | 7/1973 | Hietanen | 356/241 |
| 3,761,177 | 9/1973 | Corse | 356/23 |
| 3,920,970 | 11/1975 | Slaker | 250/572 |
| 4,026,414 | 5/1977 | Ellinger | 250/578 |
| 4,055,382 | 10/1977 | Ziekman et al. | 356/241 |
| 4,131,365 | 12/1978 | Pryor | 356/387 |
| 4,139,779 | 2/1979 | Ehrat | 356/71 |
| 4,165,939 | 8/1979 | Woodrow et al. | 356/394 |
| 4,195,904 | 4/1980 | Yamashita | 350/506 |
| 4,199,258 | 4/1980 | Dau | 356/378 |
| 4,253,768 | 3/1981 | Yaroshuk | 356/237 |
| 4,281,931 | 8/1981 | Chikama | 356/375 |
| 4,305,661 | 12/1981 | Pryor et al. | 356/241 |

FOREIGN PATENT DOCUMENTS

| | | | |
|---|---|---|---|
| 2718802 | 11/1978 | Fed. Rep. of Germany | 250/223 B |
| 12377 | 2/1978 | Japan | 356/237 |
| 924396 | 4/1963 | United Kingdom | 364/507 |
| 637705 | 12/1978 | U.S.S.R. | 356/241 |

OTHER PUBLICATIONS

Mayes et al., "High-Speed Image Capture For Mechanical Analysis", IBM Tech. Disc. Bull., 12-1973, pp. 2169–2171.

Vesnina et al., "Instrument for Measuring the Depth of Scratches on Inside Surfaces of Tubes", Optical Technology, 1-1972, pp. 33–35.

Primary Examiner—William H. Punter
Attorney, Agent, or Firm—Larson and Taylor

[57] ABSTRACT

A method of determining physical characteristics of a surface. Light or other electromagnetic radiation is directed onto a first portion of a surface and the reflected radiation is received such as by a photodiode. The radiation is also directed onto at least two further portions of the surface and located on either side of and proximate to the first portion. The radiation reflected by the further portions is also received. The radiation reflected from the first portion is compared with the radiation reflected from the two further portions. The radiation and comparison steps are repeated and the comparisons are used to determine a physical characteristic of the surface, such as the presence of one or more flaws. In another embodiment, light or other electromagnetic radiation is used to determine object dimension, such as bore dimension.

28 Claims, 19 Drawing Figures

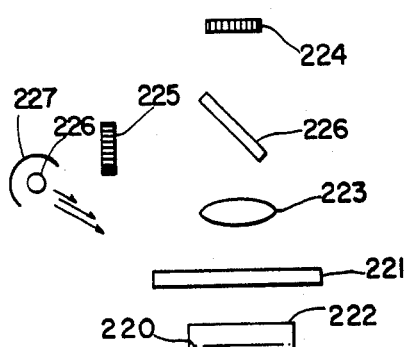
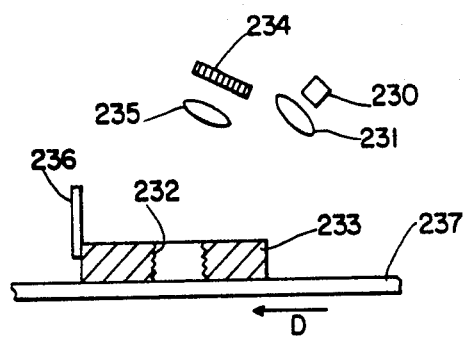
FIG. 11
FIG. 12
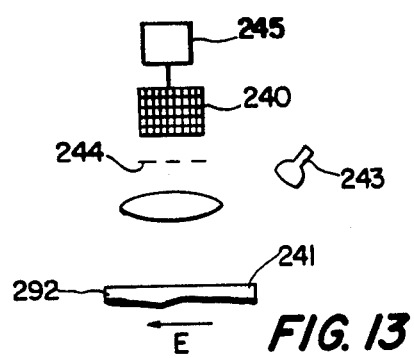
FIG. 13

METHOD AND APPARATUS FOR DETERMINING PHYSICAL CHARACTERISTICS OF OBJECTS AND OBJECT SURFACES

This is a continuation, of the application Ser. No. 15,792, filed Feb. 27, 1979, now U.S. Pat. No 4,305,661.

DISCLOSURE DOCUMENT

This invention relates to subject matter disclosed in Disclosure Document No. 059,719, filed Apr. 14, 1977.

FIELD OF THE INVENTION

The present invention relates to apparatus and methods for determining physical characteristics of an object or object surface. More particularly, the invention relates to such apparatus and methods for determining such physical characteristics as surface flaws including holes, bumps, depressions, surface configuration and shape, surface and object size, and the like.

There are a number of methods and procedures described in the patent literature which relate to detection of surface flaws and other physical characteristics of surfaces and objects. Representative United States patents include U.S. Pat. Nos. 3,761,186, 3,749,496, 3,983,388, 4,055,382, and 4,072,427.

It is an object of the present invention to provide apparatus and methods which are reliable, durable and capable of rapidly inspecting surfaces and objects to determine physical characteristics such as surface flaws, and the like.

BRIEF SUMMARY OF THE INVENTION

The foregoing and other objects which will become apparent to those of ordinary skill in the art in view of the disclosure which follows, are achieved in accordance with a first embodiment of the present invention, by providing a method for determining a physical characteristic of a surface which includes the steps of directing electromagnetic radiation onto selected portions of a surface, receiving radiation reflected therefrom, comparing the radiation reflected from a first selected surface portion with radiation reflected from at least two further selected surface portions, the further selected surface portions being located on either side of and proximate to the first selected surface portion, and determining a physical characteristic of the surface based on the comparison.

Apparatus for carrying out the foregoing method includes means for directing electromagnetic radiation onto selected portions of the surface, means for receiving radiation reflected from the surface, means for comparing the radiation reflected from a first selected surface portion with the radiation reflected from at least a second selected surface portion and a third selected surface portion, the second and third selected surface portions being spaced apart and proximate to the first surface portion, and means for determining a physical characteristic of the surface based on said comparison.

In another embodiment, there is provided a method of obtaining dimensional information concerning a cylindrical surface which includes providing a mirror member having a mirror surface adjacent a surface of the object, directing electromagnetic radiation onto the mirror surface and thence onto the object surface, whereby the radiation directed onto the surface is reflected back to the mirror surface, and analyzing the radiation reflected back from the surface and mirror to obtain dimensional information concerning the object. Apparatus suitable for carrying out this method includes mirror means having a mirror surface adapted to be placed into adjacency with an object surface, means for directing electromagnetic radiation onto the mirror surface and thence onto the object surface whereby the radiation directed onto the surface is reflected back to the mirror surface, and means for analyzing the radiation reflected back from the surface and mirror to obtain dimensional information concerning the cylindrical surface.

In a further embodiment, there is provided a method for determining the physical characteristics of the outer surface of an elongate object which includes the steps of providing a mirror member having a mirror surface in the form of a conical surface of revolution and having an aperture at its apex and passing through the mirror member, positioning an elongate cylindrical object in the aperture in axial alignment with the mirror surface, directing electromagnetic radiation in an axial direction onto the mirror surface and thence onto the outer cylindrical object surface, and analyzing the radiation reflected back from the object surface to determine a physical characteristic of the object surface. Apparatus suitable for carrying out this method includes a mirror member having a mirror surface in the form of a conical surface of revolution and having an aperture at its apex and passing through the mirror member, means for positioning an elongate cylindrical object in the aperture in axial alignment with the mirror surface, means for directing electromagnetic radiation in an axial direction onto the mirror surface and thence onto the outer cylindrical object surface whereby the radiation impinging on the object surface is reflected back to the mirror surface, and means for analyzing the radiation reflected back from the object surface to determine a physical characteristic of the surface.

DETAILED DESCRIPTION

Preferred embodiments of the invention are described in the detailed description which follows, including the drawings in which:

FIG. 3b is a schematic timing diagram depicting exemplary waveforms at various locations in the circuit depicted in FIG. 3a.

FIG. 11 is a diagrammatic side elevation view, partly in section, of a portion of a seventh embodiment of the invention;

FIG. 12 is a diagrammatic side elevation view, partly in section, of a portion of an eighth embodiment of the invention;

FIG. 13 is a diagrammatic side elevation view, partly in section, of a portion of a ninth embodiment of the invention;

Figure 1:
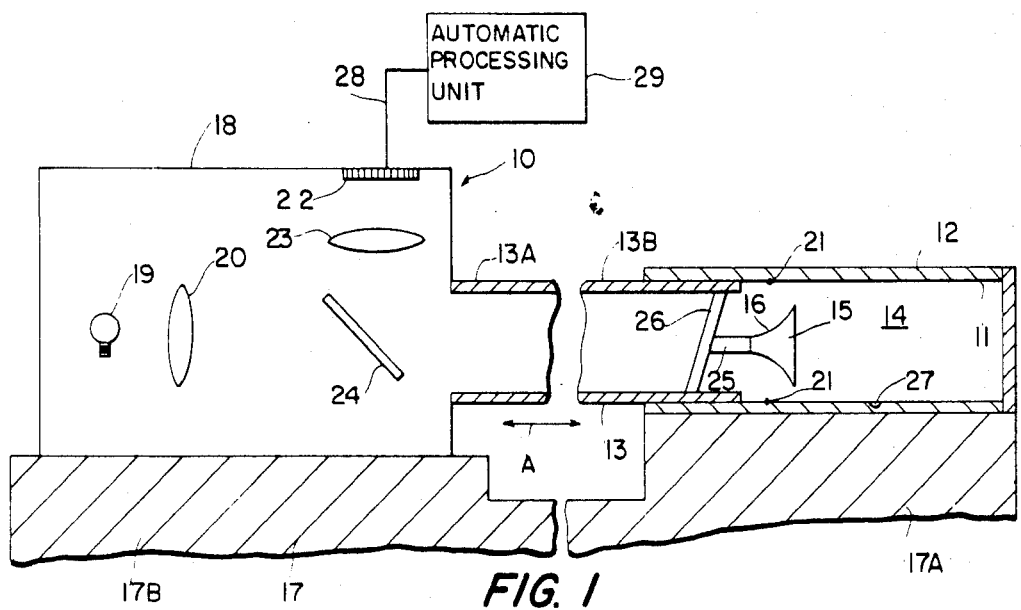
FIG. 1 is a diagrammatic, side elevation view, partially in section, of a first embodiment of the invention.

A device 10 for inspecting a bore in accordance with the invention is shown in FIG. 1. The bore surface 11 which is to be inspected is the inner cylindrical surface of a tube 12. Tube 11 may be any part, such as a hydraulic brake cylinder, or the like and a simple cylindrical tube is shown for simplicity. It will be assumed for purposes of illustration that the bore is made by a machining operation and it is desired to determine if there are any flaws in the surface in the form of holes resulting from casting or machining. Device 10 includes a probe 13 which is movable axially of bore 14 of tube 12 as shown by arrow A in FIG. 1. The probe is movable in any convenient manner such as by moving the entire device 10 horizontally in the sense of FIG. 1 or by moving the part 12 relative to the device 10. At distal end the probe carries a mirror 15 having a mirror surface 16 which is in the form of a conical body of revolution. The mirror surface is preferably parabolic or substantially so. The probe is arranged in any convenient manner to move coaxially a pre-determined position in the tube bore 14. For example, the device may include a table or bed 17 which supports both the tube 12 and a housing 18 which supports probe 13. The device includes suitable clamps or other means to secure housing 18 and tube 11 in the general position shown such that probe 13 may move axially within bore 14. To this end, the device preferably includes means for adjusting the position of the probe and/or housing 18 relative to the position of the piece undergoing inspection. For example, portion 17A of table 17, on which tube 12 is fixedly supported may be movable vertically and horizontally at right angles to arrow A to align the bore and probe. The piece under inspection is positioned adjacent housing 18 such that the probe, can move into the bore to an extent necessary to inspect the desired portion of surface 11. In the simplest case, probe 13, secured to housing 18, is moved in by motorized slide 17B in the direction of arrow A under the influence of any suitable control means, now shown.

Light from a source 19 is directed through lens 20 down through the hollow probe and onto parabolic mirror surface 16 of mirror 15 carried at the distal end of probe 13. Light source 19 is conveniently a conventional halogen bulb. The mirror is designed to focus the light onto bore surface 11 in the form of a bright circumferential ring denoted as 21 in FIG. 1. The bright ring of light is reflected back down the probe tube by mirror surface 16 and is imaged upon a light detector array 22 by means of a lens 23 via a beam splitter 24. The light detector array in this embodiment is preferably circular in view of the circular format of the light reflected from bore surface 11. An example of a suitable array is a circular, self-scanning photodiode array. For example, a commercially available circular array with a mean diameter of 0.28 inches and having 720 photodiode elements arranged on one half degree centers is suitable. Mirror surface 16 is preferably designed to focus the incident light on the bore surface to provide an intense bright ring of light which is readily detected by the photodiodes in array 22. Mirror 16 is secured in position at the distal end of probe 13 in any convenient manner such as by a mounting member 25 secured to mirror 16 and to a transparent member 26, preferably glass, fixedly mounted in tube 13. Glass member 26 is preferably inclined to the probe axis to reduce reflection of incident light back to detector array 22.

In use, test piece 12 is positioned on table portion 17A such that probe 13 moves coaxially within bore 14. In use, as the probe is axially translated through the bore length, each successive portion of the bore length is sequentially scanned by the array which can operate, typically, with speeds of several thousand scans per second. This allows an extremely quick scan of the bore with considerable detail. For example, in the case of a 7 inch bore having a diameter of 1.7 inches, the bore can be scanned in about 1 second with every detector of the array reading a zone of approximately 0.007 inches × 0.030 inches (approximately) on any one scan. Obviously, resolution can be increased or decreased by using different detector arrays and by changing the lens magnification. For example, in the system described above, the bore diameter is 1.7 inches and the diameter of the circular array is 0.28 inches. If the diameter of the array were increased to, say 1.7 inches, and the width of the individual detectors kept the same, the number of detectors would increase from 720 to over 4000 and resolution would increase correspondingly. Of course, in that instance, lens 23 would be adjusted to image the reflected light on the larger array. Lens 23 and the other optical elements of the system are thus preferably adjustable to accomodate various applications of the device.

The light reflected from the bore surface readily displays physical features such as dirt, holes, depressions, ridges, bumps, and the like present in the illuminated area of the bore surface. These show up as zones of differing intensity in the reflected light. The size and intensity of those zones depends, of course, on the extent and nature of the physical characteristic on which the focussed light is incident. In the illustrated case, in which the bore is machined, it is desired to detect flaws in the form of depressions such as porosity pit 27 shown exaggerated in size in FIG. 1. These flaws are indicated by a substantial reduction in reflected light. In some instances, such as where the flaw is large, the defect can be detected by examination of the reflected light by the unaided eye. For example, holding the probe in fixed position with the light incident on a defect such as hole 27, a dark spot in the reflected ring of light can be readily seen by, for example, imaging the reflected light ring on a viewing screen. An object of the invention, however, is to provide a rapid and dependable method of inspecting bores and the like and this is accomplished, in accordance with the present invention, by automatically examining the reflected light in an appropriate processing unit in which a comparison is made between the light reflected from a portion of the bore surface with the light reflected from a known standard bore surface and/or further portions of the bore surface at locations on either side of and proximate to the first mentioned portion of the bore. In the usual case, the portion under investigation is the zone from which reflected light is received by an individual detector in an array, although the portion under investigation may be longer. Further, in the usual case, the further portions used for comparison purposes each constitute a zone on the bore surface from which reflected light is received by at least one individual detector. It is important that the analysis of the reflected light takes into account variations in light level around the bore surface due to various factors such as dirtiness of the bore, mis-alignment of the probe within the bore (e.g. not truly co-axial) or other characteristics of the bore which are not flaws of the type desired to be detected but which nevertheless can cause changes in reflected light level. Accordingly, the electrical output signals 28 from detector array 22 are directed into automatic processing unit 29.

As mentioned above, photo detector array 22 is commercially available. These arrays are available in many configurations and can be readily obtained commercially.

Most detector arrays employ solid state, light sensitive elements such as photodiodes, although other elements such as photosensitive transistors could be used. Photo array video cameras having a square matrix of 128×128 photosensitive elements are the General Electric Model TN 2200 and TN 2201 video cameras. Other commercially available photo arrays include linear arrays and rectangular matrix arrays. Furthermore, any type of video camera can be used, including the continuous raster sweep type that is used in conventional television. Naturally, the specific circuitry in a particular automatic processing unit has to be compatible with the particular type of video detector.

Figure 2B:
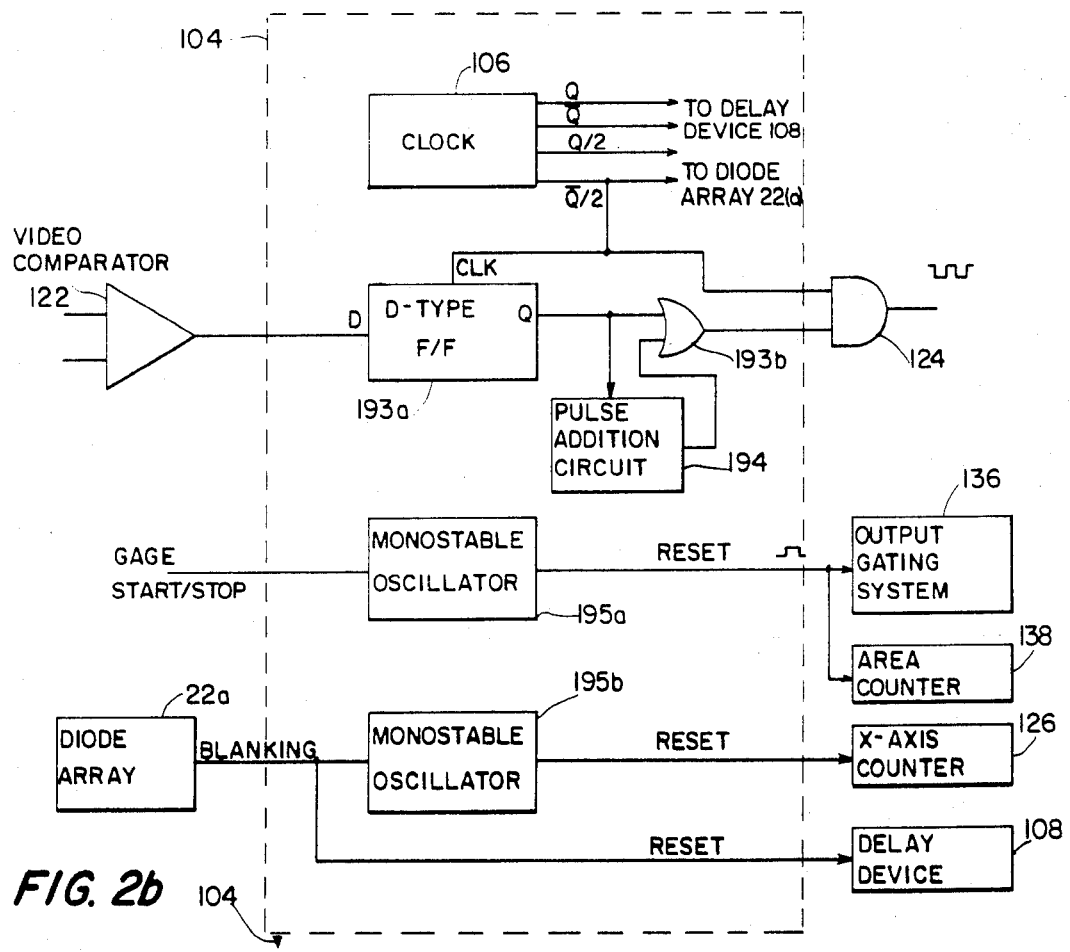
FIG. 2b is a more detailed, electrical schematic block diagram of part of a system controller usable in the circuit depicted in FIG. 2.
Figure 2:
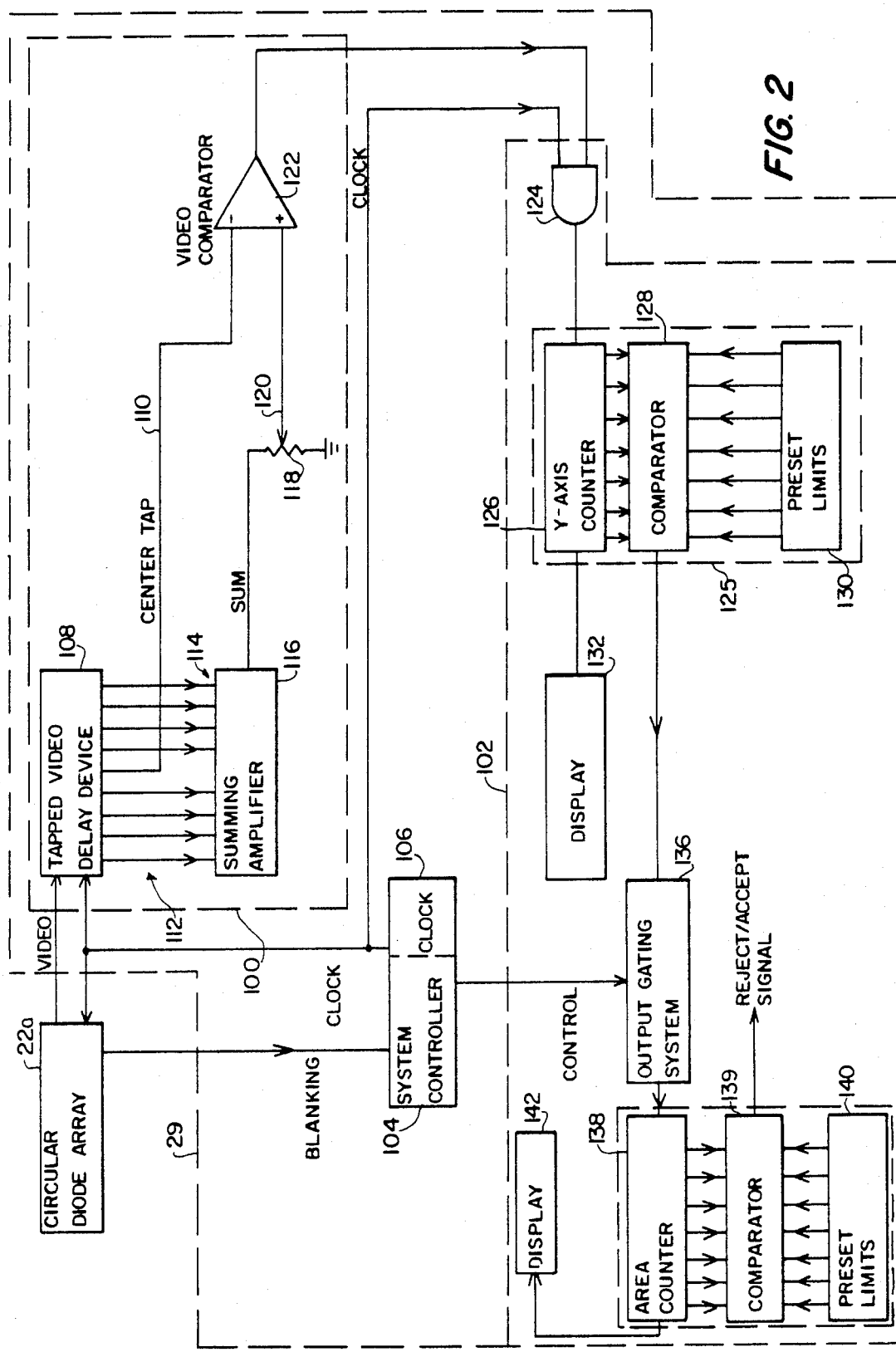
FIG. 2 is an electrical schematic block diagram of one embodiment of an automatic processing unit according to the invention.

With reference now to FIG. 2, there is depicted a schematic circuit diagram for one embodiment of an automatic processing unit 29 usable with the apparatus depicted in FIG. 1 for detecting flaws in the surface of a bore. Automatic processing unit 29 includes a comparison circuit 100 for comparing the radiation reflected from a surface portion of the bore with the radiation reflected from a plurality of surface portions on either side of the selected portion and adjacent thereto, a determining circuit 102 connected to the output of comparison circuit 100 for determining the presence of a flaw and for producing an output indicative thereof, and a system controller 104 which includes a clock 106 in combination for providing the timing and control signals for processing unit 29 and for the detector array 22. A typical frequency for clock 106 is 5 MHz, and in order to provide very rapid signal processing, comparison circuit 100 is preferably comprised of analog electronic components.

Comparison circuit 100, in turn, is comprised of a serial in, parallel out, analog delay device 108 that is connected to the output of detector array 22, denoted 22a in FIG. 2 for the specific embodiment employing a circular photodiode array camera. Analog delay device 108 in a presently preferred embodiment is a 32 stage tapped analog delay commercially available as TAD-32.

This device provides a plurality of clock controlled analog delay lines that effectively sample and store analog signals and is the rough analog equivalent to the well known family of digital shift registers such as the 7495 4-bit shift register. Connected to the output of analog delay device 108 are a central conductor or center tap 110, a plurality of upstream conductors or taps 112 and an equal number of downstream conductors or taps 114. Upstream taps 112 and downstream taps 114 are connected to a summing amplifier 116 which can be comprised of one or more operational amplifiers, such as a 3403 or an LM301A. The output of summing amplifier 116 is connected to a voltage divider resistor 118 having a variable center tap 120, which in turn is connected to the plus or reference terminal of a video comparator 122. The other end of resistor 118 is connected to ground and thus resistor 118 can be adjusted to provide any weighted average of the sum of the voltages which are available on the upstream and downstream taps 112 and 114 of analog delay device 108. The negative or variable input to video comparator 122 is connected to center tap 110. Video comparator 122 can be any conventional voltage comparator circuit such as the commercially available LM311 voltage comparator which has a very low input current, is operable over a wide range of supply voltages, and has an output that is compatible with standard digital circuits such as RTL, DTL, TTL, and MOS circuits.

System controller 104 is comprised of conventional elements and circuits to provide overall circuit control in accordance with the requirements of a particular application of the present invention and as well as the requirements of the other components in automatic processing unit 29 and array 22. For example, in a bore scanning application of the present invention as depicted in FIG. 1, and as described hereinabove, a circular array of photodiode cells is used to capture the annular ring of light reflected from the surface of the bore being inspected. The light incident on each individual cell produces or results in a current proportional to the intensity of the light. The individual cell current is converted into a corresponding cell voltage by the internal camera circuitry and is made available at the serial video output of the camera when the cell is selected. Serial selection of the cells occurs in a well known fashion in response to the clock pulses from clock 106. As a result of the internal configuration of the conventional Reticon circular diode array discussed above, the last cell in the array is not electrically connected to the first cell in the array and several timing pulses are required in order to switch between them. This requirement of the video camera is accomplished without advancing the information in delay device 108 and without the making of false comparisons or determinations by system controller 104 by using a blanking signal produced by array 22 to disable the other components of automatic processing unit 29 for the requisite number of clock pulses.

It should be apparent that the voltages on center tap 110 can be compared with a plurality of different averages of the remaining output lines from analog delay device 108. In addition, the number of delay lines in analog delay device 108 can be varied and, depending upon the particular application, can be less than, equal to, or greater than the number of light cells in camera 22a. It should also be apparent that the reference level voltage supply to video comparator 122 can be set with resistor 118 to be either higher or lower than the expected video level voltage on center tap 110. For example, in some typical applications of the present invention, the interior of the bore surface being investigated would produce a lower video signal for a defect or flaw in the surface because less light would be reflected therefrom or the reflected light would be scattered. Thus, the reference level voltage input to video comparator 122 would be set for a lower threshold level so that an output from video comparator 122 would result whenever the voltage on center tap 110 was lower than the weighted average of the voltages appearing on upstream taps 122 and downstream taps 114. Finally, it should be apparent that by judiciously selecting the analog components in comparison circuit 100 that the output from video comparator 122 can be obtained in a fraction of a millisecond. This rapid speed for making mathematical computations and comparisons is not presently available in conventional inexpensive digital circuits and microcomputers, although with special programming it may be available in larger main frame general purpose digital computers.

The output from video comparator 122 of comparison circuit 100 is transmitted to determining circuit 102 as a binary signal which, for the sake of convention, will be considered to be a positive signal if the voltage output from the central storage cell of analog delay device 108 and available on center tap 110 is less than the weighted average of the voltage outputs from the upstream and downstream cells and available on upstream taps and downstream taps 112 and 114, and is considered to be zero if the reverse is true. Thus, video comparator 122 can be thought of as an analog threshold comparator whereby it either has an output (which can also be called a "one" or "true") or it does not (which can also be called as "zero" or "false"), depending upon whether the illumination striking the central photodiode of an array of photodiodes is less than or greater than the weighted average of the illumination striking the remaining photodiodes in that particular array, respectively.

The output from video comparator 122 is fed to the input of a conventional 2 input AND gate 124, the other input of which is from clock 106. The output from AND gate 124 is, in turn, coupled to the input of a first evaluation circuit 125 that is comprised of a counter 126, a comparator 128, and a storage device 130. Counter 126 receives the signal from AND gate 124 and can be a conventional synchronous up/down, digital counter such as integrated circuit number 74192, in which case AND gate 124 is directly connected, for example, to the COUNT-UP input thereof. Comparator 128 compares the output count from counter 126 with a predetermined, preset limit stored in storage device 130. Comparator 128 can be, for example, a commercially available digital comparator such as integrated circuit number 7485, and storage device 130 can be either a hard wired circuit or a programmable circuit, such as a further integrated circuit chip 74192. The output from counter 126 is also connected to a display device 132 so that the count can be visibly available to an operator. Obviously, display 132 could also be a recording device to temporarily or permanently record the count per unit time per device being inspected so that an indication of the location of the defects can be obtained.

The output from comparator 128 is a signal which indicates whether the count has exceeded the preset limits and thus an indication that there is a discontinuity or flaw in the surface of the bore being inspected. Because of the sensitivity of the apparatus, even small particles of dirt will be detected and indicated by video comparator 122. In addition, electrical noise, optical aberrations, and other sensitivities in the system will indicate the presence of a surface aberration at the output of video comparator 122 when none actually exists. Finally, certain surface aberrations are so small that they can be ignored. Because of the foregoing considerations, storage device 130 is adjusted to contain an appropriate preset limit so that only the surface aberrations which are of a certain, predetermined size need be considered.

In certain embodiments of the invention, the output from comparator 128 could be used as an article accept or reject signal which can be coupled to a conveyor on which the article being inspected is being moved past the detector of the present apparatus and can cause the conveyor either to past along an accepted article or discharge it as a rejected article. However, in the embodiment depicted in FIG. 1, the signal from comparator 128 is sent to still another evaluation circuit 134 so that the axial length of the flaw in the bore surface can be considered before rejecting the article. Connected between evaluation circuit 125 and evaluation circuit 134 is an output gating system 136 coupled to and controlled by system controller 104. Output gating system 136 is comprised of conventional, digital TTL integrated circuit chips which are hard wired together to provide a logic system so that the output from evaluation circuit 134 will be pursuant to preselected criteria. In addition, gating system 136 provides a means by which system controller can disable evaluation circuit 134 during system start up or when starting a second scan.

Evaluation circuit 134 is comprised of the same components as evaluation circuit 125, namely a counter 138, a comparator 139, and a storage device 140 for containing a preset limit. The output from comparator 139 is also the output from automatic processing unit 29 and is a reject/accept binary signal. Obviously the output from comparator 139 could be gated in an OR gate so that in a further embodiment of the invention, either an "X-axis" flaw indication from comparator 128 or an "area" flaw indication from comparator 139 can be used to reject an article being inspected.

Figure 2A:
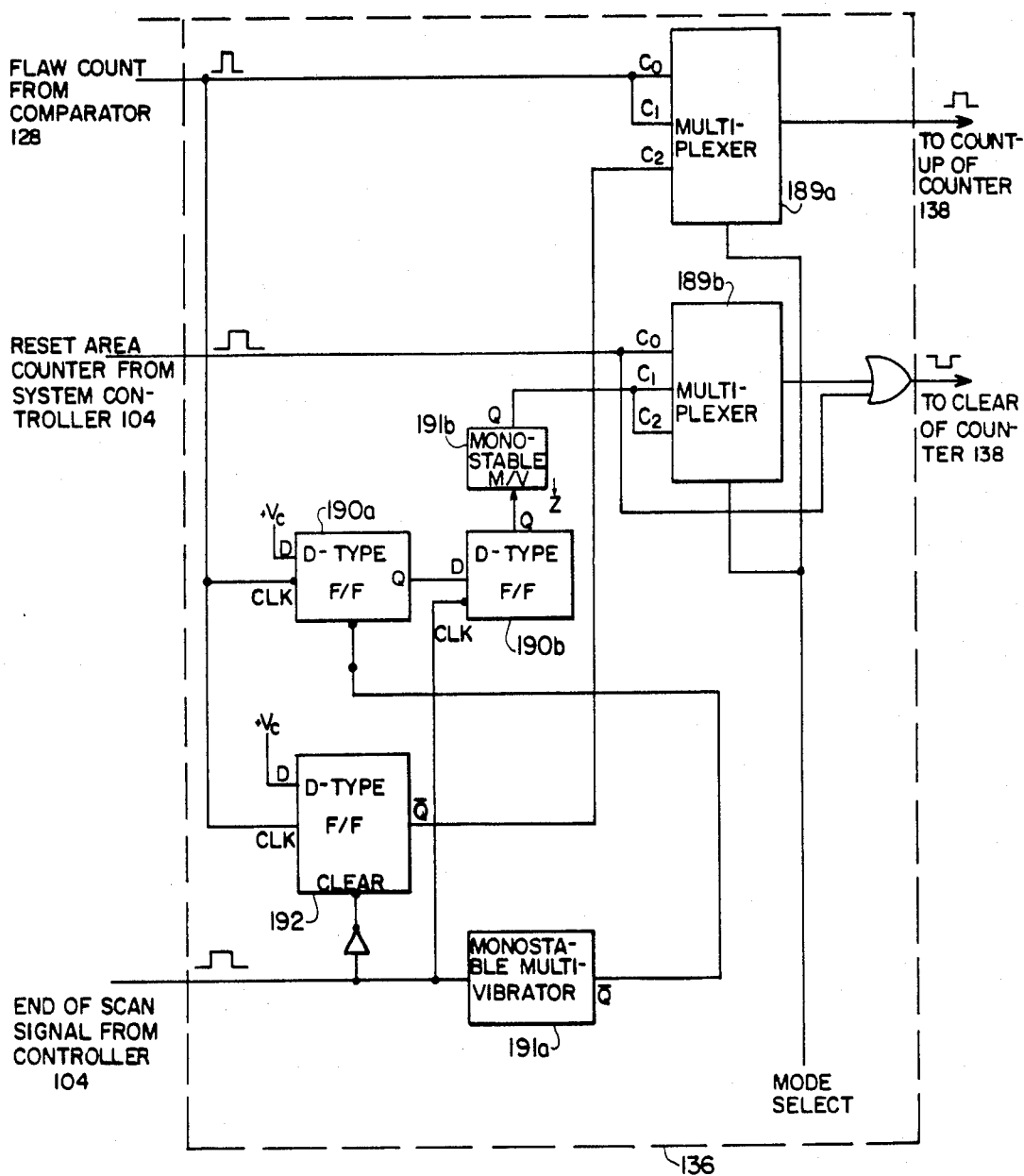
FIG. 2a is a more detailed electrical schematic block diagram of the output gating system depicted in FIG. 2.

The logic which permits evaluation circuit 134 to operate under different modes is contained in output gating system 136, as mentioned above, and one example thereof is depicted in FIG. 2a. Three modes of operation are selectable. For example, a first mode of operation is one whereby output gating system 136 merely operates as a switch and passes a signal from comparator 128 directly to area counter 138. In this mode of operation, an article will be rejected if it has a predetermined number of flaw indications on the same or different surface rings irrespective of whether those rings are contiguous or not. Thus an article will be rejected whenever a predetermined number of flaws are detected. An exemplary second mode of operation from output gating system 136 permits an article to be rejected only after the counting of a predetermined number of contiguous surface rings having one or more flaws per ring. As mentioned above, the size of the ring is the size of the surface swept by one scan of the annular photodiode array. In this mode of operation, output gating system 136 would clear the count in area counter 138 whenever a complete scan of the circular diode array did not result in the indication of a flaw as determined by the output from comparator 128. The number of contiguous scans having a flaw needed to reject an article is determined by storage device 140. In the second mode of operation, it can been seen that automatic processing unit 29 is rejecting an article only when the flaw in the surface being investigated has a predetermined axial length equal to the predetermined number of consecutive scans of diode array required to trigger the rejection of the article. In an exemplary third mode of operation, only the number of scans which have one or more flaws are counted, and an article is rejected only when the preset number of scans with flaws has been exceeded, irrespective of the total number of flaws.

As shown in FIG. 2a, two programmable multiplexers, 189a and 189b permit a signal from one of their respective inputs, $C_0$, $C_1$, or $C_2$, to be passed to their respective outputs, depending upon the mode select signal (which is actually a 2-bit signal). Multiplexers 189a and 189b can be, for example, integrated circuit chips number 74153. The output from multiplexer 189a is fed to the "count up" input of area counter 138 and the output from multiplexer 189b is fed to the "clear" input of area counter 138. If the "$C_0$" input is selected, then area counter 138 is a straight counter, counting all of the pulse outputs from X-axis comparator 128 and being reset (i.e., cleared) at the end of the entire inspection cycle (or earlier if the article is rejected) by a signal generated by system controller 104. If the "$C_1$" input is selected, then area counter 138 still counts each pulse from X-axis comparator 128, but is now cleared at the end of each scan that does not result in a flaw signal being generated by X-axis comparator 128. The logic to accomplish this consists of two serially connected D-type flip-flops 190a and 190b (e.g., integrated circuit chips number 7474), the former having its clock input connected to the output of X-axis comparator 128, its clear connected to the $\overline{Q}$ output of a first monostable multivibrator 191a (e.g., integrated circuit chip number 74123) that is triggered by the end of scan [EOS] signal generated by system controller 104, and its D input tied high. Flip-flop 190b has its D input connected to the Q output of flip-flop 190a and is clocked by the EOS signal. The Q output of flip-flop 190b is connected to both the $C_1$ and $C_2$ inputs of multiplexer 189b via a second monostable multivibrator 191b. Finally, in the third mode of operation the $C_2$ input multiplexer 189a is selected and this input is fed by the $\overline{Q}$ output of a third D-type flip-flop 192 that has its D input tied high and is clocked by the output from the X-axis comparator 128. The clear input is connected to the EOS signal through an inverter. Thus, as the end of every scan, flip-flop 192 is cleared setting its $\overline{Q}$ output high. Because counter 138 in this example is a 74192, it counts only upon the application of a negative going pulse and thus the application of a clear signal to flip-flop 192 does not produce a count. However, should a scan indicate one or more flaws (i.e., a pulse is emitted by X-axis comparator 128), then the high at the D input to flip-flop 190 will be clocked to the Q output and a low to the $\overline{Q}$ output, resulting in a zero, or negative going pulse, being applied to area counter 138. Subsequent pulses from comparator 128 will not produce another negative pulse from the $\overline{Q}$ output of flip-flop and thus only one pulse can be transmitted to area counter 138 for each scan. Hence area counter 138 counts only the number of scans having flaws and not the total number of flaws. Also, like in the aforementioned second mode of operation, area counter 138 is cleared after every scan which does not produce a flaw indication and thus an article is rejected only if there are a predetermined number of contiguous scans which indicate flaws.

Obviously, other modes of operation are possible and can include other combinations of counting and clearing area counter 138. In addition, by simply using a counter (e.g. a series of R/S flip-flops or a serial-in serial-out shift register) between X-axis comparator 128 and area counter 138, a predetermined number of flaws will have to be counted per scan or a series of contiguous scans, depending on whether area counter is cleared after a scan which does not have a flaw, in order to produce a count in area counter 138.

As mentioned above, the particular circuit elements in circuits which together comprise system controller 104 vary according to the particular application of the present invention as well as the requirements of the other components in automatic processing unit 29 and the particular video camera used. With reference to FIG. 2c, system controller 104 for operation with an annular photodiode array in a bore scanning application is depicted. Clock 106 is comprised of conventional components which can either include a crystal or merely two back-to-back monostable oscillators such as are available in integrated circuit chip 74123. An exemplary output frequency from clock 106 for use with the present components is 425.5 KHz. Because the TAD used in delay device 108 requires twice the frequency of the diode array, the output from the clock oscillator is divided by two by using a conventional divide-by-two R/S flip-flop.

As indicated in FIG. 2b, the output from video comparator 122 is conditioned by a D-type flip-flop 193a and an OR gate 193b before the signal is fed to AND gate 124 to modulate the output of clock 106. The other input to OR gate 193b is a pulse addition circuit 194 which can merely consist of gated back-to-back monostable oscillators such as integrated circuit chip No. 74123, so that the two counts lost as a result of biasing video comparator 122 can be made up. Finally, as also indicated in FIG. 2b, the reset signals from both the gauge start/stop (which indicates when an article is in position for the investigation of its surface to be commenced), and the blanking signal from diode array 22a are conditioned with monostable oscillators 195a and 195b so that an accurately shaped pulse can be produced. Thus, it can be seen that the logic circuit for the particular application of the present invention in the bore scanning application is extremely simplistic and obviously well known to those of ordinary skill in the art. A variation of system controller 104 for use with a linear array is discussed hereinbelow with respect to FIG. 3b.

In operation, automatic processing unit 29 as depicted in FIG. 2, when enabled, continuously clocks circular diode array camera 22a, video delay device 108, and AND gate 124. System control 104 also receives the gauge start/stop signal from a transducer (not shown) which indicates that probe 13 has entered the bore being investigated. The gauge start/stop signal is used to generate a further signal in system controller 104 which in turn zeros area counter 13. Output gating system 136 permits any signals from evaluation circuit 125 to be transmitted to evaluation circuit 134 in accordance with the preselected mode of operation of output gating system 136.

Alternatively, system controller 104 can control the operation of clock 106 to permit its signals to be passed to the aforementioned elements when enabled by the further transducer signal indicating that the probe has entered the bore. In still another embodiment, further logic in system controller 104 can disable output gating system 136 until a predetermined number of output signals from corresponding photodiode cells has been clocked into video delay device 108. Otherwise, video comparator 122 would indicate a flaw when, for example, only the first two or three output signals from the photodiode cells are clocked into the first few stages of video delay device 108 and there would be no correct signal in the central stage of video delay device 108 with which to make a valid comparison.

Then after a certain number of clock pulses, 720 clock pulses in an exemplary embodiment, circular diode array 22a is completely scanned and the circuitry in the commercially obtained array generates a blanking signal, for example, of 4 clock pulses to permit the "retrace" of array 22a, as mentioned above. During the 4 retrace clock pulses, system controller 104 disables video delay device 108 and X-axis counter 126 by sending a reset signal thereto because no valid data is coming in during that period. Because diode array 22a is a physically complete annular array, the first photodiode cell is physically contiguous to the last photodiode cell in the array, there is no need to initialize video delay device 108 upon the completion of a scan of diode array 22a. As mentioned above, because of the use of analog components in comparison circuit 100, a complete scan of a 7 inch long bore can be accomplished in less than a second.

Figure 3:
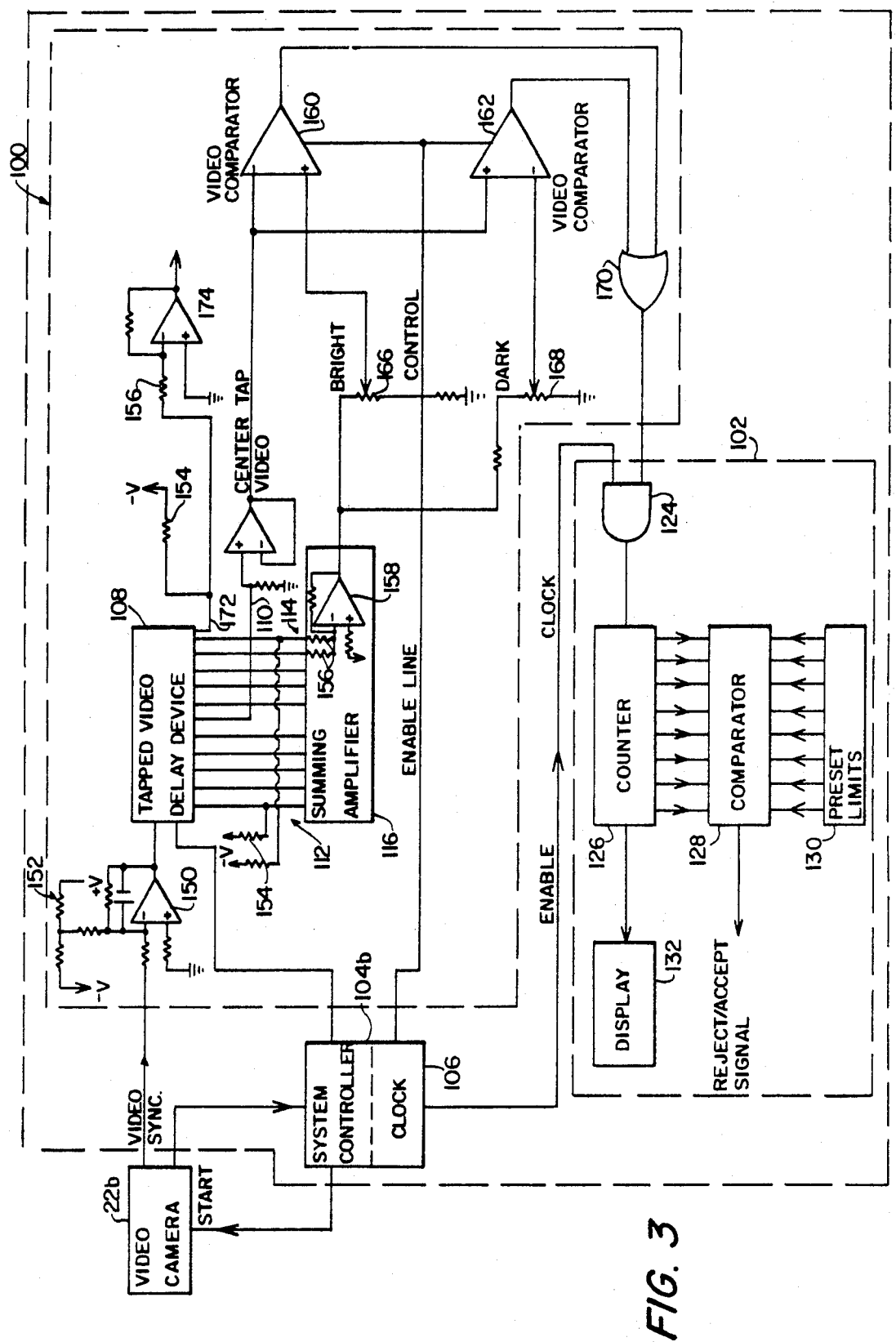
FIG. 3 is an electrical schematic block diagram of a second embodiment of an automatic processing unit according to the invention wherein exemplary analog circuit components are depicted in the comparison circuit.

With reference now to FIG. 3, a second embodiment of an automatic processing unit 29 is depicted for exemplary use with a linear photodiode array in a video camera 22b. The same numerals will be used for those components in FIG. 3 which are the same as the components in FIG. 2. However, FIG. 3 does have greater detail than FIG. 2 with respect to the depiction of the use of operational amplifiers at various points in comparison circuit 100. A modified system controller 104b with a clock 106 provides an initialization or start signal to video camera 22b and receives a sync pulse therefrom for a complete hand-shaking interconnection. The video signal from a particular photodiode cell of video camera 22b is connected to the negative input of a conventional input operational amplifier 150 that is in a feedforward compensation configuration. An input bias rheostat 152 is also connected to the negative input of operational amplifier 150 so that the limited voltage range can be accommodated for the TAD-32A device used as video delay device 108. Input operational amplifier 150 can be any general-purpose operational amplifier such as an LM301A, a device which provides a high degree of accuracy and lower noise in a high impedance circuit and has low input current requirements.

Comparison circuit 100 as depicted in FIG. 3 is also comprised of the same video delay device 108 and summing amplifier 116 as in FIG. 2, but they are shown in greater detail. Each of the output taps 110, 112 and 114 of video delay device 108 is tied to a negative supply voltage with a resistor such as resistors 154. In addition, each tap of upstream taps and downstream taps 112 and 114 are connected through an input resistor 156 (only two of which are shown) to the negative input of an operational amplifier 158, configured in the circuit as a summing amplifier. Center tap 110, which is not connected to summing amplifier 116, is indirectly connected in parallel to the negative inputs of two video comparators 160 and 162, which can also be operational amplifiers LM311 like video comparator 122 in FIG. 2. However, in order to provide impedance matching between video delay device 108 and voltage comparators 160 and 162, center tap 110 is connected to the positive input of a coupling operational amplifier 164 configured as a fast voltage follower. Coupling amplifier 164 can be a conventional operational amplifier number 3403.

The other, reference inputs of video comparators 160 and 162 are connected in parallel to the output of summing amplifier 116 through respective voltage dividing resistors 166 and 168 so as to provide an upper and a lower threshold, respectively, for the video signal from the central photodiode cell, as mentioned above. Unlike the video comparator 122 in FIG. 2 which does not use its strobe input, video comparators 160 and 162 have their corresponding strobe inputs connected to system controller 104b so that comparison circuit 100 can be disabled at that point. The outputs from video comparators 160 and 162 are fed to the respective inputs of a 2-input OR gate 170 so that there is an output from comparison circuit 100 whenever either the upper video threshold or the lower video threshold has been exceeded. In this regard, it is noted that nicks in the surface can produce a brighter surface reflection while cracks in the surface generally produce a darker surface in comparison with the surrounding surface portions.

Determining circuit 102 in FIG. 3 is identical to one-half of determining circuit 102 and operates as explained above in connection therewith. Therefore, no further description of the determining circuit 102 in FIG. 3 need be provided.

Video display device 108 in FIG. 3 is also depicted with a feedforward output 172 which is coupled to the last stage thereof and is connected to the negative input of an amplifier 174 that is configured in the circuit as a simple inverting amplifier and which can also be a 3403 operational amplifier. Feedforward output 172 is also tied low through a tie down resistor 154. As the name implies, the purpose of feedforward output 172 is to couple video delay device 108 to a further video delay device for purposes explained hereinbelow.

Figure 3A:
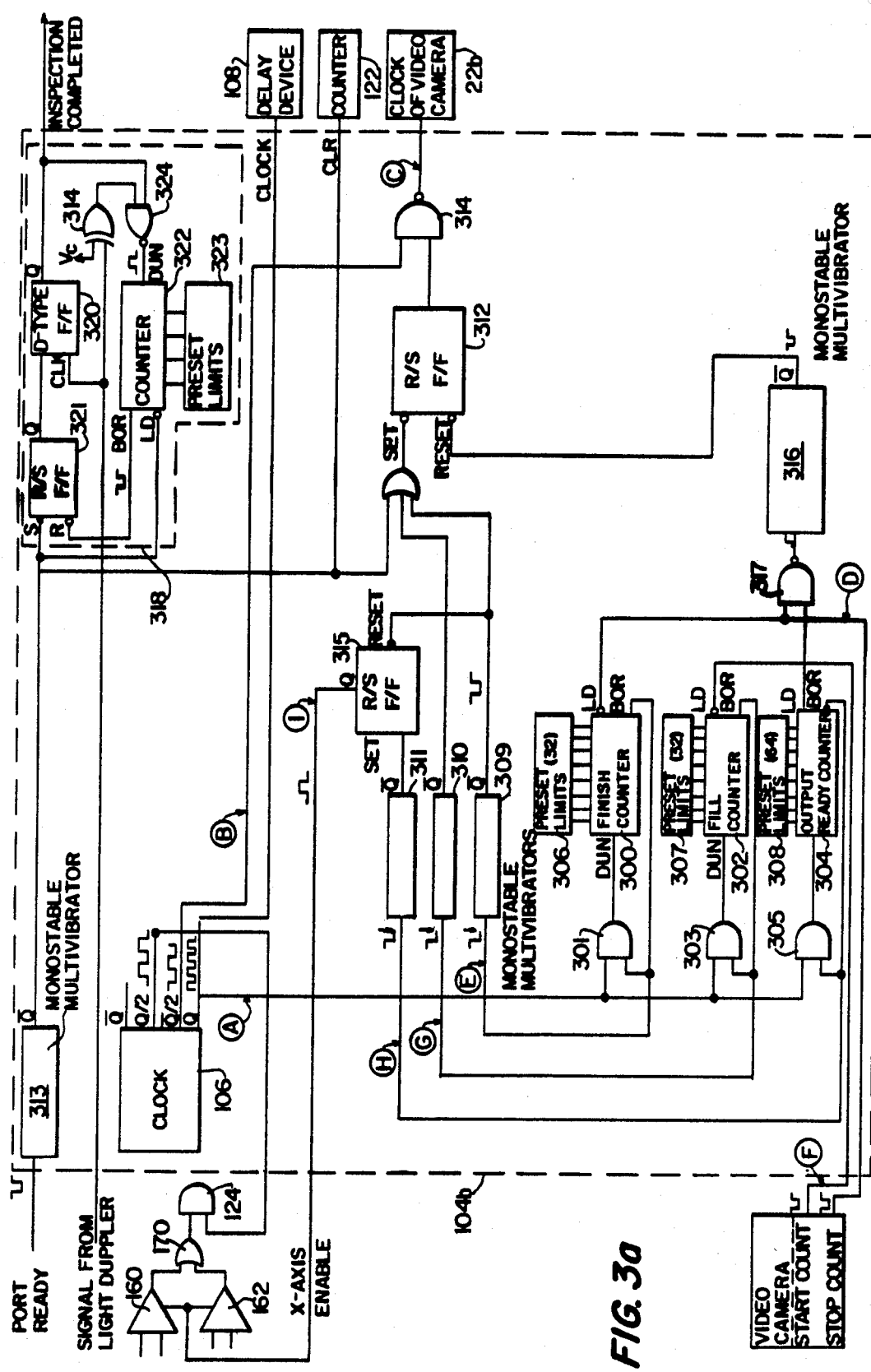
FIG. 3a is a more detailed, electrical schematic block diagram of some major components of a system controller usable in the circuit depicted in FIG. 3.

With reference now to FIG. 3a, an embodiment of system controller 104b is depicted. The clock 106 produces a normal clock output which drives a clock of delay device 108 and clocks the DOWN COUNT input of three counters, a finish counter 300, a fill counter 302 and an output ready counter 304 through three respective, two-input AND gates 301, 303, and 305, the other input to which is from the BORROW output of the respective counter. Counters 300, 302, and 304 can, for example, be conventional intergrated circuit chips No. 74LS193. Because the borrow line goes low when the counter has been counted down to all zeros, coupling the borrow line to the input of the respective AND gates 301, 303 and 305 results in locking-out the clock input to the counter once the counter has been counted down to zero. Each counter has respective pre-set limits located in input storage devices 306, 307 and 308 for counters 300, 302 and 304. Storage devices 306, 307 and 308 contain, for example, a hard wired "count" of 32, 32 and 64, numbers which are exactly double the desired number of array cell clock pulses, but equal to the numbers of delay device pulses. Fill counter 302 and output ready counter 304 are loaded with their stored inputs with a low going pulse emitted at the beginning of a scan from video camera 22b. Finish counter 300, on the other hand, is loaded by the low going pulse of a stop count similarly provided by video camera 22b.

The BORROW output from counters 300, 302, and 304 are respectively fed to the input of three monostable multivibrators 309, 310 and 311 which are wired to trigger on the low going edge of a pulse. As should be evident, before the counters are loaded, the BORROW line is low and as soon as the counters are loaded with their respective pre-set limits, the BORROW output goes high. However, it is only when the BORROW output goes low again (i.e., the counter has been completely counted down) that the low going pulse triggers the respective monostable multivibrator. The $\overline{Q}$ outputs from monostable multivibrators 309 and 310 are connected to the SET input of an R/S flip-flop 312. A third input of the SET input is from the part ready signal provided when a part is ready to be inspected and which is connected to the input of the flip-flop through the $\overline{Q}$ output of pulse-shaping monostable multivibrator 313. The Q output of master R/S flip-flop 312 is fed to one input of a two input NAND gate 314, the output of which provides the clocking signal for video camera 22b. The other input to NAND gate 314 is the $\overline{Q2}$ clock signal.

The enable signal for comparators 160 and 162 is developed at the Q output of an enable R/S flip-flop 315. Enable flip-flop 315 is set from a negative going pulse emitted by monostable multivibrator 311, which, as stated above, is in turn triggered by a negative signal from output ready counter 304 at its BORROW output. On the other hand, enable flip-flop 315 is reset (i.e., a "0" at the Q output) by the negative going output from the $\overline{Q}$ output from monostable multivibrator 309. Master flip-flop 312 is reset by the negative going signal from the $\overline{Q}$ output from a monostable multivibrator 316 which is triggered at its positive going signal input from the output of a two-input NAND gate 317. NAND gate 317 is fed by the start count signal and the stop count signal. Thus, it can be seen that master flip-flop 312 is reset upon every start count signal and every stop count signal.

Figure 3B:
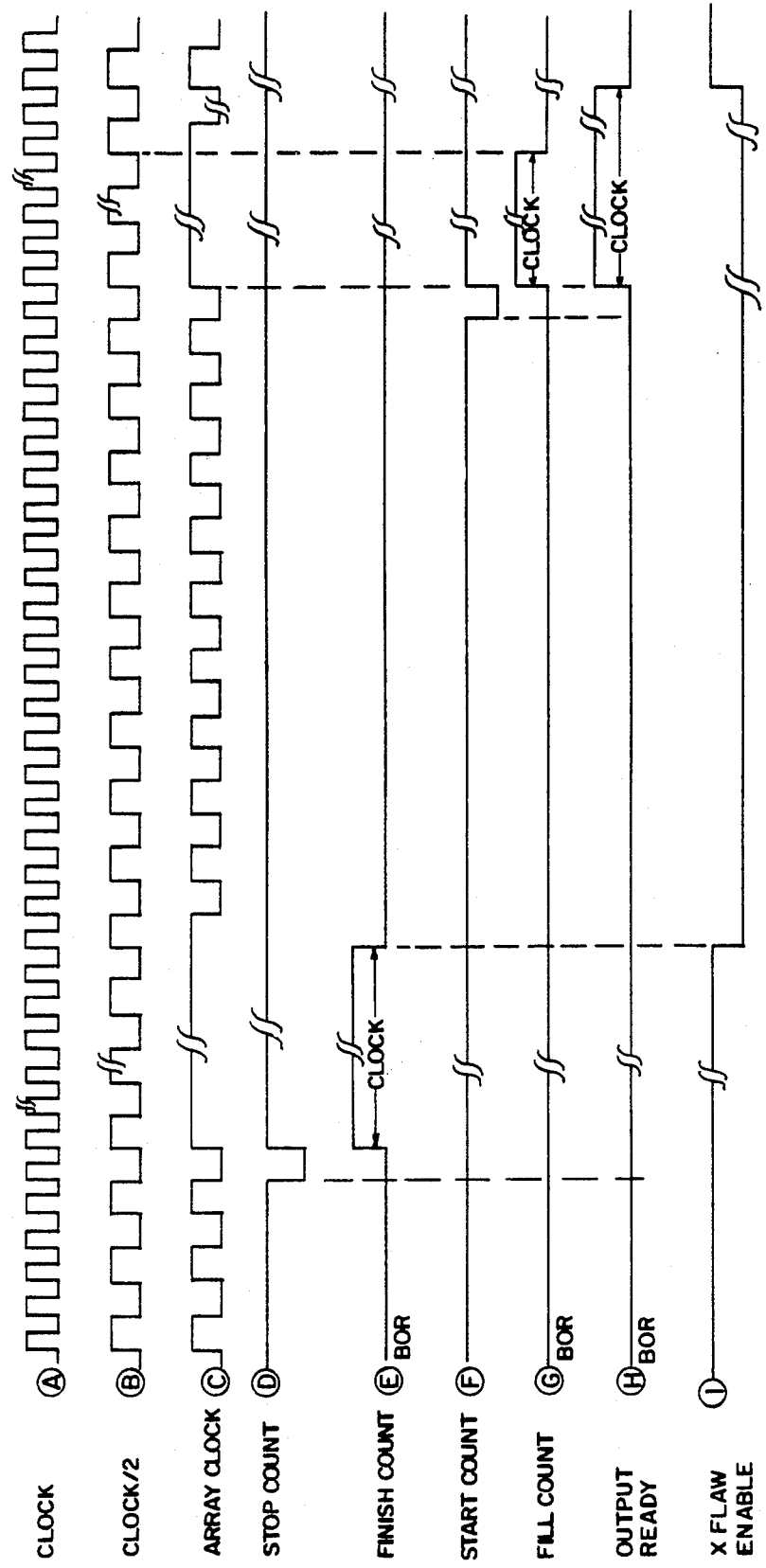

With reference to FIG. 3b depicting a timing diagram with the corresponding signals taken from the points lettered in FIG. 3a, it can be seen that by the judicious selection of the SET signals and the RESET signals to master flip-flop 312 and enable flip-flop 315, the clocking of the video camera is not dependent upon the clocking of flaw data from comparison circuit 100 to determining circuit 102.

In one particular use of the present invention, a valve stem is inspected about its cylindrical circumference. The valve stem is mounted for rotation on a platform which also contains a light chopper for producing in a conventional manner light pulses indicative of the angular position of the support and hence of the valve stem being inspected. This signal is used by an inspection completed circuit 318 which is part of system controller 104b. Inspection completed circuit 318 receives a signal from the light chopper through an EXCLUSIVE-OR gate 319, the other input of which is tied high. Thus, the output from gate 319 will be active or high only when there is no signal from the light chopper. The inspection completed output of circuit 318 is produced by a D-type flip-flop 320 which receives its clock input from the light chopper and its D-input from an R/S flip-flop 321. R/S flip-flop 321 is set by the negative going $\overline{Q}$ output from part ready monostable multivibrator 313 and a reset signal from a counter 322. Counter 322 is configured similarly to counters 300, 302 and 304 and thus has a hard-wired, preset limit in an input storage device 323, a LOAD input also from the output of part ready monostable multivibrator 313, a COUNT DOWN input and an output on its BORROW output. The COUNT DOWN input of counter 322 receives a signal from the output of a two-input NAND gate 324, one input of which is from the Q output of flip-flop 320 and the other input of which is from the output of EXCLUSIVE-OR gate 319. The negative going pulse on the BORROW out of counter 322, when the counter has been counted down to zero from the pre-set number from storage device 323 as a result of pulses from the light chopper, is coupled to the RESET input of flip-flop 321.

Operation of inspection completed circuit 318 is similar to that of the three timing counters used to control the enable and master flip-flops 315 and 312. As soon as a part ready signal is received from an appropriate transducer (not shown), R/S flip-flop 321 is SET and a "1" is fed to the input D-type flip-flop 320 and the pre-set limit in device 323 (e.g. ten) is loaded into counter 322. The first positive going pulse from the light chopper will clock the "1" input to the Q output of flip-flop 320 and the first negative going pulse from the light chopper will result in a "1" being sent from EXCLUSIVE-OR gate 319 to one input of NAND gate 324. Since a "1" had previously been sent to the other input of NAND gate 324 when flip-flop 320 output went high, a negative pulse is sent to counter 322. As soon as this pulse goes high, which occurs when the next positive pulse is transmitted by the chopper, counter 322 will be counted down by one. When counter 322 is counted down to zero in this manner, a negative pulse will be sent to flip-flop 320, resetting it and in turn providing a low pulse to the "Q" output of flipflop 320. The next positive going pulse from the light chopper will clock the zero through to the output of flipflop 320 and thus give an indication that the inspection is completed.

The operation of the automatic processing unit 29 depicted in FIG. 3, is slightly different than the operation of the automatic processing unit 29 depicted in FIG. 2 because a linear photodiode array is used in the video camera of FIG. 3 whereas a circular photodiode array is used in the video camera in FIG. 2. The main difference is manifested in the initializing routine described above and the rountines between the subsequent scans of the array. However, in both systems, the TAD delay device must be clocked twice for each time the photodiode array is clocked. System controller 104b initially clocks video camera 22b one time as soon as an enable signal is received, thereby indicating that the probe is in position to commence the investigation of the particular article. The first clock signal is also sent to video delay device 108 so that the output from the first photodiode cell is received by the first delay stage and transferred by this first clock pulse to the second delay stage. However, video delay device 108 is then clocked an additional 16 times (assuming that video delay device 108 comprises a TAD 32A) as determined by fill counter 302 without video camera 22b being clocked so that the signal from the first photodiode of the linear array appears on the first 16 delay stages of video display device 108. Then, the clock pulses from clock 106 are sent by system controller 104b to both video camera 22b and video delay device 108 so that the next 16 photodiode cells, as determined by output ready counter 304, are loaded in a serial fashion and stored in video delay device 108. So far, video comparators 160 and 162 have not been enabled so that there is no output therefrom. After video delay device 108 has been clocked 32 times, however, video comparators 160 and 162, as well as AND gate 124, are enabled to begin the comparison operation of comparison circuit 100. From here, the entire photodiode array (which can be comprised of as many as 1,728 photodiode cells), is scanned until the last photodiode cell is reached. At this point, in response to a signal generated by the commercially available array system, controller 104b stops clocking video camera 22b, but continues to clock video delay device 108 so that the output from the last photodiode cell is loaded 16 times into video delay device 108 as determined by finish counter 300. After the signal from the last photodiode cell of the array has been loaded 16 times into video delay device 108, video comparators and determining circuit 102 are disabled so that the flaw processing of the signals is disabled, and another scan with prior initialization of the photodiode array is initialed as described above. The purpose of loading the outputs from both the first photodiode cell and the last photodiode cell of the linear array is to prevent a fall-off of the optical system on either edge of the viewing field. This procedure is necessary because the first photodiode cell and the last photodiode cell of the video array are physically spaced apart and are not contiguous as they are in an annular photodiode array.

As mentioned above, the last delay stage of video delay device 108 in either FIG. 2 or FIG. 3 can be coupled through an amplifier 174 to the first stage of a further video delay device (not shown). The purpose for serially connecting the two video display device is to overcome the practical limitation in number of delay stages of the commercial devices currently available. The second delay device can be run at the same clock rate as the first delay service, thereby only extending the total number of delay stages by a factor of two. However, the averages from the first delay device from summing amplifier 116 and a corresponding divider network and the two delay devices can be clocked at different rates with the result of a multiplying effect. For example, if the second delay device is run at a quarter of the clock rate of the first delay device, and each delay device has 32 stages, the net effect is a combined delay device having 128 stages.

Figure 4:
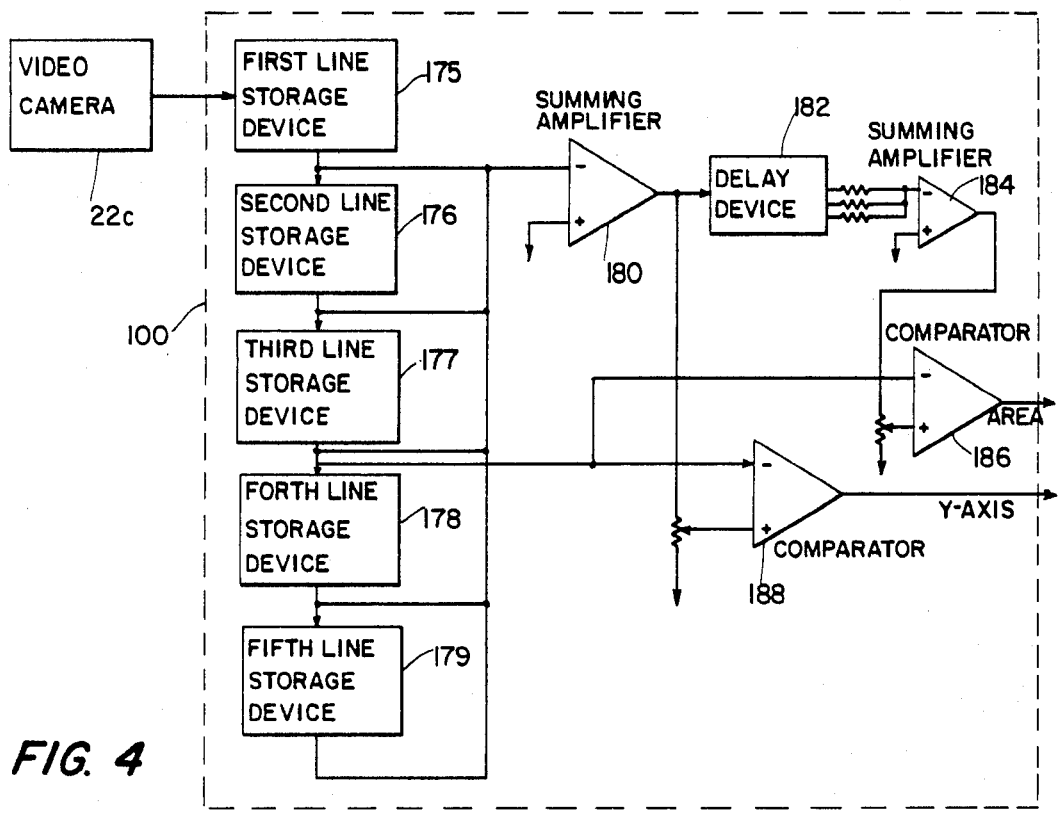
FIG. 4 is an electrical schematic block diagram of a third embodiment of an automatic processing unit according to the invention.

Referring now to FIG. 4, a further embodiment of an automatic processing unit 29, denoted 29c, is depicted which provides a matrix of signals from a plurality of scans and thus has the capability of providing an average of the sequential outputs from the same photodiode cell. Thus, this circuit can produce an average signal from a surface extending in the direction of probe travel.

Automatic processing unit 29c provides analysis of a surface scan of the entire photodiode array of camera 22c and produces a line of signals. Each scan of the array of photodiodes results in a line of signals being produced. This line of signals would be representative of a surface that is perpendicular to the direction of travel of probe 12. A representation of the surface along the axis of probe travel can be obtained from the signals produced by the same photodiode cell in the linear array during several successive scans. If the direction of the surface on each scan is selected as the X-axis of a coordinate system, then the Y-axis would be defined as the "direction of the signals from the same cell during successive scannings of the linear photodiode array. The principle of operation of the comparison circuit 100c depicted in FIG. 4 is based on the foregoing considerations.

Comparison circuit 100c is comprised of a plurality of serially connected line storage devices, such as the five line storage devices 175, 176, 177, 178, and 179, depicted in FIG. 4. However, it should be obvious that there is no particular reason for limiting the number of line storage devices to only the number depicted in FIG. 4, the number five being chosen merely for exemplary purposes. Each line storage device can be a serial analog delay device number SAD512 or 1024 commercially available from Reticon Company. The SAD device is essentially a "bucket brigade" of charge coupled devices which can be externally clocked so as to transfer the charge from one storage cell to the next storage cell. The output of all of the storage devices are tied together and coupled to the negative input of a conventional summing amplifier 180, which can be similar to amplifier 158 depicted in FIG. 3. The output from summing amplifier 180 is connected through a voltage dividing resistor to the input of a delay device 182, which can be the same as the TAD-32 used as video delay device 108. Delay device 182 outputs are all summed in a further summing amplifier 184, the output of which is coupled to the variable signal or negative input of a comparator amplifier 186 through a voltage dividing resistor. Comparator amplifier 186 is the same as or can be similar to video comparator 128 of FIG. 2. The reference input of comparator 186 is the output from third line storage device 177. Thus, the output from comparator 186 represents an area comparison. A Y-axis comparison is obtained by coupling the output from summing amplifier 180 to the reference input of a further comparator 188, which can be similar to comparator 186. The variable or negative input to comparator 188 is obtained from the output of third line storage device 177. The output from comparison circuit 100c is sent to a determining circuit (not shown) for further processing of the signal similar to that described above with respect to FIGS. 2 and 3.

The automatic processing units described above are readily adapted to various further embodiments of the invention as will be apparent from the illustrations which follow.

Figure 5:
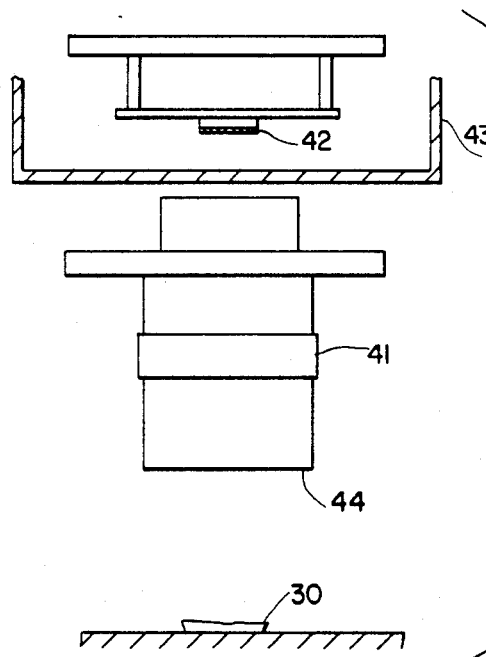
FIG. 5 is a diagrammatic side elevation view, partly in section, of a second embodiment of the invention.
Figure 6:
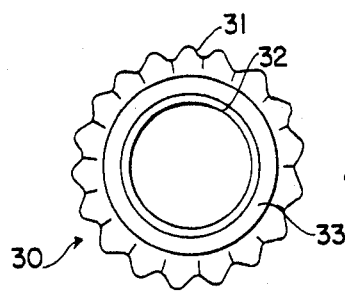
FIG. 6 is a diagrammatic plan view of an inverted bottle cap.

The device of FIG. 5 is adapted to inspect bottle caps of the type having a serrated edge such as those widely used for soft drinks, beer, and the like. A typical cap is illustrated in FIG. 6. Cap 30 includes a serrated edge portion 31, a seal portion 32, and a flash portion 33. Defects in each of these areas may cause a non-secure closure resulting in leakage etc. These caps are mass-produced in large quantities at a rapid rate and an automatic inspection system, capable of identifying defective caps at normal production rates, is provided in the device of FIG. 5.

All of the optical components of the device of FIG. 5 are contained in a suitable cabinet (not shown) mounted over the inspection station 40. A glass window (not shown) in the bottom of the cabinet allows light from a flash tube (not shown) to illuminate the cap 30. A lens 41 positioned in-line above cap 30 forms the cap image onto the face of a photodiode array 42 which is mounted in a sub-enclosure 43.

The flash tube (not shown) is circular and positioned around a shielding tube 44 extending downward from the lens. The sensor 22 comprises a self-scanning circular photodiode array as described above in connection with FIG. 1. The array consists of 720 separate photodiodes, or elements, arranged in an annular ring concentric with the lens 41, flash tube, and cap 30. The element spacing is one half degree. The inside and outside radii of the array are 0.136 inch and 0.144 inch respectively so that the length of each element in the radial direction is 0.008 inch. Each element is 0.0008 inch wide, and the element spacing at the inner radius is 0.0012 inch. Light falling between elements is collected by the nearest element, since the entire area is photosensitive.

Lens 41 forms the cap image onto the array so that the image size is smaller than the cap, since the array itself is smaller. This reduction factor is variable so that any zone between the seal and the serrations of cap 30 can be imaged onto array 42. This is accomplished by physically moving the lens/array combination (i.e. the whole optical head) closer to or farther away from the cap by any suitable means, not shown. Thus, the array size remains fixed, and the image size is varied appropriately.

Knowing the physical dimensions of cap 30 and the array geometry, it is possible to calculate what physical dimension on the cap is being covered by the sensing area on the array. For example, the approximate means seal diameter is 0.81 inch. Since the mean array diameter is 0.28 inch, the optical reduction is 0.81÷0.28=2.9. Therefore, the image of the cap for seal inspection is reduced 2.9 times from the actual cap size. Since the array elements are 0.008 inch long radially, and spaced every 0.0012 inch at the inner radius, each element covers 0.008×2.9=0.023 inch radially, and 0.0012×2.9=0.0035 inch circumferentially. For other zones, the same calculations can be performed, resulting in the following table:

| Zone | Approx. Dia. on Cap | Optical Reduction | Length Covered Radially by one Element | Length Covered Circumferentially by one Element |
| --- | --- | --- | --- | --- |
| Seal | .81 | 2.9 | .023 | .0035 |
| Flash | .94 | 3.4 | .027 | .0041 |
| Serration | 1.18 | 4.2 | .034 | .0050 |

A scale and pointer (not shown) are preferably provided on the outside of the cabinet to indicate where the cabinet should be positioned for each zone of inspection. The focusing ring of the lens is adjusted for each zone.

The electrical output from each photodiode is proportional to the intensity of the light it receives, up to the saturation point. A prefectly uniform surface (e.g. a good seal) will produce the same output for each element. A surface irregularity will result in some deviation from uniformity. For example, a seal gap will cause a bright spot on the cap due to the underlying metal being more exposed. The photodiodes which cover this area will then show a higher signal output. By applying suitable electronic thresholds to the signal as explained above in connection with FIG. 1, the deviation can be detected and quantified as to the severity of the flaw. It is preferred to process the signals from detector array 42 in the manner described above in connection with the embodiment of FIG. 1. Defects or flaws in the seal area, the flash area, and the serrated edge area are readily detected in this manner.

In an alternative embodiment, detector array 42 may include three concentric annular arrays, one for each area of the bottle cap being inspected. This would enable the simultaneous inspection of all those areas of interest and would avoid the necessity of moving lens 41.

It will be apparent that the embodiment of FIG. 5 can also be used to scan the lips of bottles and any other ring shaped symetric object where flaws around ring shaped areas is a problem.

Figure 7:
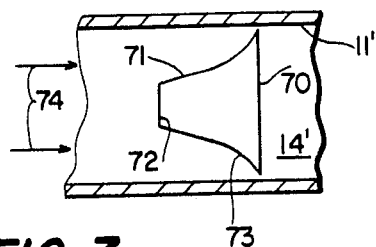
FIG. 7 is a diagrammatic side elevation view, partly in section, of a portion of a third embodiment of the invention.

The parabolic configuration of the mirror surfaces shown above in the bore scanner of FIG. 1 has the advantage of providing an intense focused ring of light on the bore surface, as well as collecting reflected light from multiple angles. However, various other mirror configurations may be used, such as the configuration shown in FIG. 7. The mirror element 70 has a two-part mirror surface 71. The first part, 72, disposed closer to the incident light 74 passing into bore 14' is reflected at a small angle onto bore surface 11' and this is incident on the bore surface as grazing incident radiation. The second part, 73, may be flat or curved as shown and is positioned to reflect light from the bore surface back down the tube to the detector array not shown. The remainder of the device and its operation may be the same as in FIG. 1. The significant difference is that the bore image which is reflected back onto the detector array is influenced by two types of radiation: grazing radiation from portion 72 of mirror surface 71 and direct radiation, which may be focused as in the embodiment of FIG. 1, from the second mirror portion 73. This arrangement results in particular effects of shadows and highlights resulting from the two types of incident radiation and may facilitate detection of specific types of flaws, such as bumps or raised portions or may facilitate in reducing the number of false rejects in a particular system.

If desired, the mirror surface can be designed to focus light on a point of the bore wall surface which is axially forward of the forwardmost portion of the mirror. This is advantageous in many instances such as in examining the bottom-most portion of a blind bore.

It will also be apparent that the mirror surface which is advanced into the bore can be replaced with a lens, such as a wide angle lens. Other optical devices, such as prisms, may also be used. The invention is particularly adaptable to the examination of small bores such as nuclear fuel tubes in which case a "train" of lenses can be used to transfer the bore image to the diode array. Alternatively, a coherent fiber optic bundle may be used. It is thus possible to inspect bores having a diameter barely larger than that of readily available fiber optic components. Moreover, since fiber optic systems may be flexible, it is possible to inspect bores which are not straight. This embodiment thus has applicability to medical diagnostic work such as cystoscopes, esophagoscopy, etc. An elegant guided-wave fiber embodiment using a monochromatic, a laser light source is further described below in connection with FIG. 14.

Figure 8:
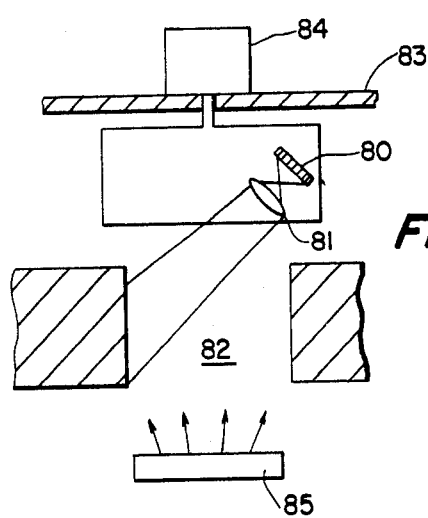
FIG. 8 is a diagrammatic side elevation view, partly in section, of a portion of a fourth embodiment of the invention.

FIG. 8 illustrates another embodiment of the invention also utilized for flaw determination in bores. This embodiment is primarily useful on bores which are relatively large in diameter relative to the depth, such as engine cylinder bores (typically 4 inches diameter and 6 inches deep). A linear scanning photodiode array 80 and lens 81, rotatably mounted on a support 83 outside the bore 82, are rotationally scanned mechanically by a motor 84 throughout 360° of the bore, viewing the bore at an angle as shown. The image plane of the diode array is tilted so as to provide a constant focus (though with somewhat varying magnification) along the total length of the bore. If the difference in magnification afforded from one end to the other end of the bore becomes a problem, this can be corrected in the flaw processing circuitry by a simple scale factor utilized on the output of the array. A light source 85 is generally located below, flooding the bore with light.

The embodiment of FIG. 8 is extremely effective in high resolution mapping of the bore without the requirement of entering the bore with a probe. It is clear that this unit when used to scan, e.g., a cylinder bore, can map out a 2048 element linear array over the total 6 inches of bore area thereby dividing it into 0.003 inch increments, approximately. When this is scanned rotationally with the array running at, e.g., a thousand scans per second, only one second is required to totally map out this bore in 0.003 inch square increments, which is extremely high resolution. Note too that in this embodiment, it is generally preferable to light from below, since the bore must be viewed at an angle. This technique is thus best used on bores which are through. Auto engine cylinder bores or pinion gear bores are good examples of this sort of application. In some instances, the part itself can be easily rotated, and the sensor fixed. A similar version for operating outside a bore without the bore physically entering it can be made using a circular diode array, such as that described above, and physically moving the sensor or using a zoom lens system.

Figure 9:
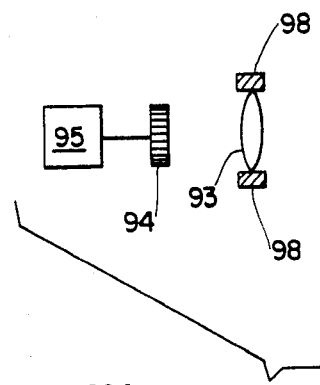
FIG. 9 is a diagrammatic side elevation view, partly in section, of a portion of a fifth embodiment of the invention.

FIG. 9 illustrates another embodiment of the invention along the line of FIG. 1 but utilized to inspect the outside diameter of a part. This system is capable of 360° scanning at high speed of a part or continuous wire for flaws or to provide its image. In this embodiment, a mirror surface 90 is preferably parabolic and similar to that to FIG. 1 except that the mirror is essentially inverted to become like the normal paraboloid mirrors of a flash-light, for example. In fact, for inspection of some parts, a flash-light mirror works quite well.

In the illustrated embodiment, the device is being used to check pharmaceutical capsules 91, which are moved in the direction of arrow B through the field of parabolic mirror 90 via a pneumatic tube 92. Sensor hardware lens 93, circular array 94, and processing on it the automatic processing unit 95, are virtually identical to that shown in FIG. 1 except for the use of mirror 96 having a hole 97 for the part to pass through. A light source such as ring 98 provides light. Because the parts have finite length, they do not get in the way of the optical path and this situation is virtually analogous to that discussed above. Machined or formed metal parts such as needle bearings, bullets etc., agricultural products such as coffee beans, etc., can also be inspected in this manner.

Figure 10:
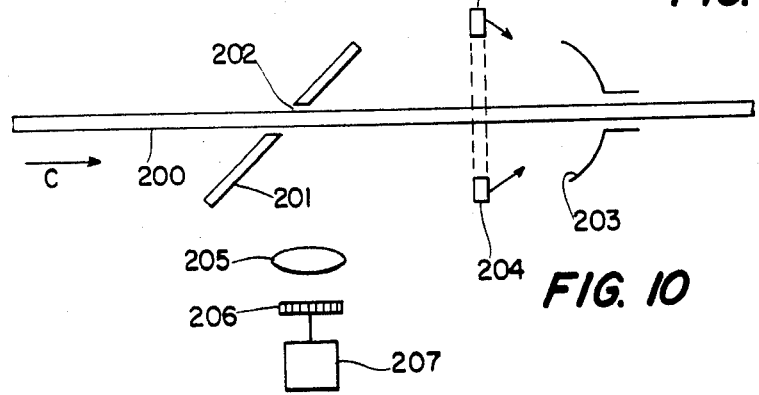
FIG. 10 is a diagrammatic side elevation view, partly in section, of a portion of a sixth embodiment of the invention.

Another major application of the invention is in the inspection of continuous products such as wire, cable, tubing etc. In this case, an embodiment as shown in FIG. 10 may be utilized. In this particular case, the wire 200 is passed, in the direction of arrow C, through a mirror 201 with a hole 202 similar to the arrangement of FIG. 9. Light is impinged upon a parabolic mirror surface 203 from a ring light source 204. The reflected light is passed through lens 205 to a circular detector array 206 and the output signal is processed as discussed above in automatic processing unit 207. It will be apparent that the product itself obscures a portion of the view of the surface of the part. The obscured portion in some cases can be essentially negligible if the wire is relatively small in diameter and the mirror 201 is able to collect the light from points around the bore such that not all of the light from the points is shadowed by the wire.

If the amount of obscuration is excessive, the system can be readily modified. For example, an annular diode array and an annular lens may be disposed co-axially with the wire and parabolic mirror 203 in which case mirror 201 is dispensed with. Alternatively, two separate systems, one on each side of the wire, and each including a mirror, lens, and diode array, may be utilized in which case each array detects a part, in this case one half, of the outer circumference of the part being inspected.

In another and simple embodiment of the invention, a linear diode array is used to image a cylindrical part which is rotated in place in front of the array or to image a sheet of material which is passed in front of the array. A particular example of this type of scanning with a linear array is shown in FIG. 11 used to find cracks or other flaws in a roller bearing 220. For normal flaws (nicks, inclusions, etc.), it is desirable to use a diffuse light source 221 (e.g. aquarium bulb) and image axially the bearing surface 222, using lens 223 and linear array 224 in conjunction with an automatic processing unit as described above. A special case exists, however, for fine cracks (e.g. under 0.001 inch). In this case, it is also desirable to use an auxiliary linear array 225, looking via beam splitter 26 at the axial circumferential zone around that in which the crack detection array 224 is operating. The two arrays are scanned together and compared with the signal from 225 providing the background level for 224. Typically, a 2× magnification lens is used, with a one mil wide array 224, and a 17 mil wide reference array 225. This arrangement is extremely effective in compensating out light level and other changes caused by bounce etc. in bearings or other parts rotated at high speeds. It can also be used anywhere that an instantaneous signal compensation is required, and can be used in conjunction with compensation in the axial direction via appropriate circuitry. For high speed applications, a halogen source 226 and elliptical mirror 227 to provide intense focused light can be used.

Another linear flaw scanning application is in scanning threads, as shown in FIG. 12. In this case, the number of threads and their pitch can be obtained, as well as any missing threads or damage. The circuitry again utilizes compensation for light level variation along the thread length. Continuous or strobe techniques can be used here in this embodiment also. As an example of the latter, a pulsed diode laser 230 and collimating lens 231 are used to illuminate the threads 232 in a nut 233. The image of the threads is formed on linear diode array 234 by lens 235. The laser is pulsed when the nut passes through a part present sensor 236 in the direction of arrow D on track 237. Both the laser and the sensing lens axes are preferably close to the thread angle if possible. A count of good threads above the floating threshold provides the answer.

The technique and circuitry of the invention is not limited only to those arrays operating in one dimension such as circular or linear arrays. A two axis or square matrix photodiode array is also amenable to the same techniques and a particularly useful one is shown in FIG. 13 wherein a square matrix array 240 is used to look at a whole scene of information with certain portions blocked out. In this particular case, it is the joint face 241 of a cylinder head 242 passing by on-the-fly underneath in the direction of arrow D. A flash gun light 242 freezes a portion to be looked at and those areas such as holes which are present normally in the head are excluded either up at the image plane with an optical mask 244 or with digital masking in the electronics. Other two-axis matrix arrays may be used, such as a TV camera. Again the same automatic processing unit 245 as described above is utilized to analyze line for line the output of the matrix of lines, and correct for light level etc.

Figure 14:
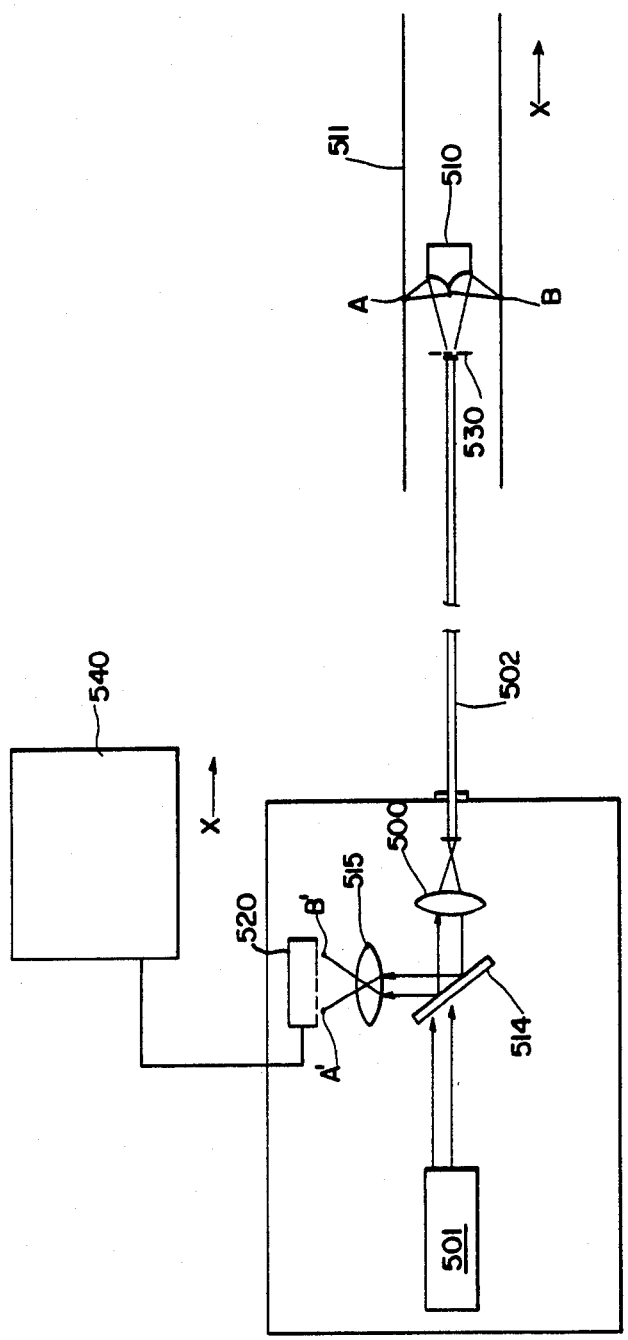
FIG. 14 is a diagrammatic side elevation view, partly in section, of a portion of a thirteenth embodiment of the invention.

FIG. 14 illustrates an embodiment of the invention providing for an extremely small diameter bore probe, mainly aimed at medical application for insertion into body passages. It also serves to illustrate the use of visual display aspects of the invention.

As shown, a bore probe along the lines of FIG. 1 is provided however, with lens-like guided wave parabolic index fiber (eg. Nippon Sheet Glass Co. "Selfoc Long Laser Guide", diameter 0.75 mm, length, 1 meter). A lens 500 matches beam from laser 501 into Selfoc fiber 502. Light emerging from the fiber is focused directly by spherical mirror of revolution 510 onto bore wall 511, which could be a human throat or vein for example. Light from the bore wall is coupled back into the fiber by the same mirror 510 and emerges to be collimated by lens 500. Via beam splitter 514, lens 515 images the result onto circular diode array 520, which in effect thereon can map out the bore surface as the probe is moved lengthwise.

It is noted that a lens 530 (dotted lines) can be used in conjunction with a conical or spherical mirror, or a fisheye can also be used. However, all lens surfaces should be well chosen and antireflective coated so as not to provide strong noise reflection into the system.

To aid in visualization of the bore wall the sampled and held output of array video data is fed to the y and z axis of a storage video display 540 with the x axis comprised by a pickoff of the movement along the bore length. This gives an extremely high resolution display since 720 data points per revolution are samples and new data can be taken every 0.001" of bore length, if desired.

Also of considerable use in flaw detection applications to display on the flaws called out by the system rather than the gray scale data.

It is particularly useful to display the instantaneous array trace on a oscilloscope together with the high and low threshold limits which one wishes to define a flaw existance.

Figure 15:
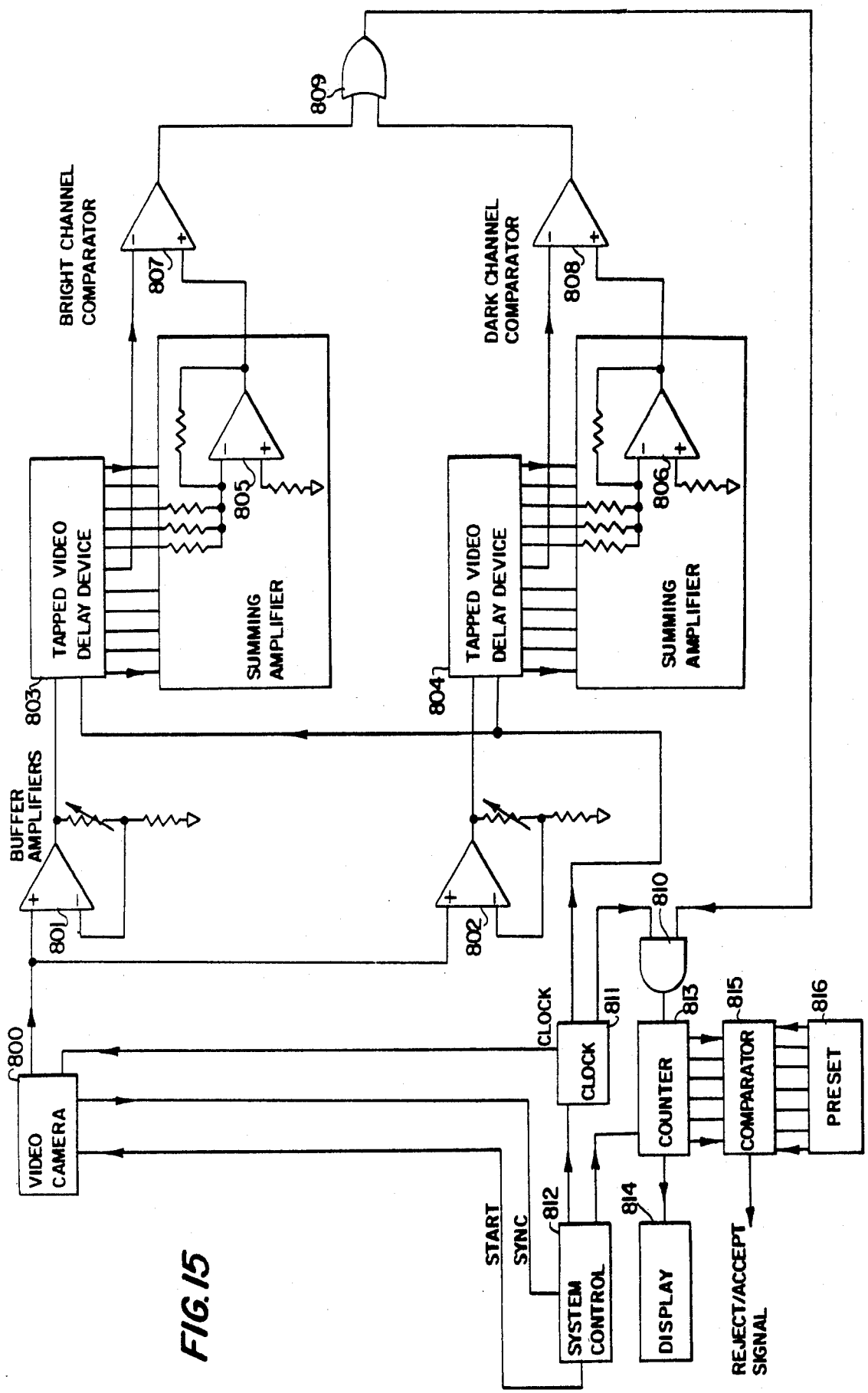
FIG. 15 is an electrical schematic block diagram of another embodiment of an automatic processing unit according to the invention.

The automatic processing unit depicted in FIG. 15 is another version of the one depicted in FIG. 3, insofar as the signal produced by video camera 800 is fed to two buffer amplifiers 801 and 802 which feed into tapped video delay devices 803 and 804. Their respective outputs are summed by summing amplifiers 805 and 806 and the sums thus produced are compared by comparators 807 and 808 respectively. The comparators send their respective flaw signals to an OR gate 809 whose output goes to AND gate 810 and the signal from clock 811 is ANDed together with the above flaw signal. The resulting signal is in the form of a series of digital count pulses in a flaw zone detected by the comparators 807, 808 and these count pulses are then directed to the counter 813 and summed during a scan of the video camera 800. At the beginning of each scan the counter 813 is set to zero so that at the end of each scan the value held by the counter corresponds to the length of the flaws as seen by the video camera 800. Comparator 815 produces a reject output when count held by the counter 813 exceeds the preset 816 input to the comparator. Display 814 is an aid to the operator of the system in case there is some doubt just why the automatic flaw processor has rejected a particular article.

The internal operation of the above automatic flaw processor is similar to the one shown in FIG. 2, that is the 16 clock pulse fill cycle and the 16 clock pulse emptying cycle are used when tapped analog delay (TAD 32 by Reticon) device is utilized in the system. The operation of the fill/empty cycles is described on pages 28 and 29 of this disclosure. The only difference between the two systems is the use of two delay devices in parallel, therefore, the clocking occurs in parallel and at the same time.

It will be apparent from the foregoing examples that the invention is capable of determining various types of physical characteristics of physical surfaces. A major application of the invention is in the detection of flaws in a surface and it is understood that the term "flaw" is used in a broad sense of including undesired nicks, dents, holes, bumps, etc., in a surface, as well as desired surface features such as threads, holes, grooves, flanges, serrations, gear teeth, and the like. In the detection of flaws, the invention may be used to distinguish between "rejects" and "accepts". The invention may also be used, however, to distinguished between objects, such as between left hand threads and right hand threads, between gear wheels having, say, 8, 12, or 16 teeth, and the like. In each of these instances, it is preferred to provide automatic equipment to distinguish between various categories of items. Accordingly, the apparatus is preferably provided with appropriate means, controlled by one or more output signals from the automatic processing units, to segregate the parts undergoing inspection into various categories. Of course, the invention is also capable of determining size, such as the diameter of a cylindrical surface including a bore surface, as described above.

The term "light" used herein is used in its broad sense to include visible light and near visible light including infra red and ultra violet.

What is claimed is:

1. A method for detecting defects in a bore surface comprising:
   illuminating a circumference of a bore surface with light, said illumination being effected by directing light onto a curved mirror to concentrate light into an intense ring of light on the circumference of said bore surface; imaging the intense ring of light reflected from the circumference of said bore onto a circular photodetector array comprising a plurality of discrete photodetector elements, said elements being capable of generating output signals responsive to the intensity of light incident thereon, said imaging being effected with optical means comprising said curved mirror which collects reflected light from multiple angles;
   scanning said circular array; and automatically analyzing the output of said array to detect defects in said bore surface.

2. A method according to claim 1 wherein said analyzing step is effected by comparing the radiation reflected from a first selected surface portion of a ring-shaped illuminated portion of said bore with radiation reflected from at least two further portions of ring-shaped illuminated portions of said bore.

3. A method according to claim 1 wherein said curved mirror is parabolic and wherein said illuminating step comprises directing substantially parallel light onto said parabolic mirror.

4. A method according to claim 1 wherein multiple scans of said array are made and wherein said bore is axially traversed relative to said intense ring of light.

5. A method according to claim 1 wherein the video data from said photodetector array is fed to a storage video display together with position data along the bore length, so as to provide a display of the part surface as it is moved relative to said photodetector array.

6. A method according to claim 5 wherein said display is provided of the defects on the surface called out by an automatic processing unit.

7. A method according to claim 2 further comprising an additional comparison step to determine the number of scans in which a defect indication has appeared.

8. A method according to claim 2 wherein said comparison is made with respect to upper and/or lower thresholds.

9. A method according to claim 2 wherein a signal delay device is utilized to allow comparison of light magnitude from an instantaneous surface portion with other portions detected by said photodetector array.

10. A method according to claim 2 wherein said comparison is made only at certain preselected areas of said surface.

11. A method according to claim 2 including the further step of providing an average of sequential outputs from the same photodetector obtained on successive scans.

12. A method according to claim 7 wherein a count of said scans is compared against a preset limit.

13. A method according to claim 12 wherein the only scans counted are those which have defects greater than a preset number.

14. A method according to claim 9 wherein an average of said other portions is used in said comparison with said magnitude of the instantaneous surface portion.

15. A method according to claim 14 wherein said average is weighted to constitute upper and/or lower threshold levels for making said comparison.

16. A method according to claim 9 incorporating the further step of disabling flaw indication output until a sufficient number of detector outputs of said array have entered said delay device.

17. Apparatus for detecting defects in a bore surface comprising:
means for illuminating a circumference of a bore surface with light, said illumination means comprising a curved mirror for concentrating light into an intense ring of light on the circumference of said bore surface;
means for imaging the intense ring of light reflected from the circumference of said bore onto a circular photodetector array comprising a plurality of discrete photodetector elements, said elements being capable of generating output signals responsive to the intensity of light incident thereon, said imaging means comprising said curved mirror which collects reflected light from multiple angles means for scanning said circular array; and
means for automatically analyzing the output of said array to detect defects in said bore surface.

18. Apparatus according to claim 17 wherein said analyzing means comprises means for comparing the radiation reflected from a first selected surface portion of a ring-shaped portion of said bore with radiation reflected from at least two further portions of ring-shaped illuminated portions of said bore.

19. Apparatus according to claim 17 wherein said curved mirror is parabolic and wherein said illuminating means comprises means for directing substantially parallel light on to said parabolic mirror.

20. Apparatus according to claim 17 wherein said scanning means comprises means for making multiple scans of said array and wherein said apparatus further comprises means for axially traversing said intense ring of light relative to said bore.

21. Apparatus according to claim 17 further comprising guided wave fiber means for transmitting, receiving, or for transmitting and receiving light from said surface.

22. Apparatus according to claim 17 further comprising means for feeding the video data from said photodetector array to a storage video display together with position data along the bore length, so as to provide a display of the part surface as it is moved relative to said photodetector array.

23. Apparatus according to claim 17 further comprising means for accumulating detected defects to provide a count for comparison to preset limits.

24. Apparatus according to claim 18 further comprising an additional comparison means for determining the number of scans in which said defect indication has appeared.

25. Apparatus according to claim 18 further comprising a signal delay device for allowing comparison of light magitude from an instantaneous surface portion with other portions defected by said photodetector array.

26. Apparatus according to claim 18 further comprising means for providing an average of sequential outputs from the same photodetector obtained on successive scans.

27. Apparatus according to claim 25 further comprising means for disabling flaw indication output until a sufficient number of detector outputs of said array have entered said delay device.

28. Apparatus according to claim 25 further comprising means for disabling said delay device during the array retrace or blanking time.

* * * * *